United States Patent
Miyoshi et al.

(10) Patent No.: US 9,125,560 B2
(45) Date of Patent: Sep. 8, 2015

(54) ENDOSCOPE SHAPE DETECTING APPARATUS

(75) Inventors: Yoshitaka Miyoshi, Hachioji (JP); Fumiyuki Onoda, Tama (JP); Hiroshi Niwa, Koganei (JP); Tomohiko Oda, Kawagoe (JP); Minoru Sato, Hino (JP); Chieko Aizawa, Hachioji (JP); Kensuke Miyake, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1029 days.

(21) Appl. No.: 11/918,389

(22) PCT Filed: Mar. 1, 2006

(86) PCT No.: PCT/JP2006/303881
§ 371 (c)(1),
(2), (4) Date: Oct. 12, 2007

(87) PCT Pub. No.: WO2006/114935
PCT Pub. Date: Nov. 2, 2006

(65) Prior Publication Data
US 2009/0030306 A1    Jan. 29, 2009

(30) Foreign Application Priority Data
Apr. 18, 2005  (JP) ................. 2005-120043

(51) Int. Cl.
*A61B 5/05*   (2006.01)
*A61B 1/005*  (2006.01)
(Continued)

(52) U.S. Cl.
CPC . *A61B 1/005* (2013.01); *A61B 1/05* (2013.01); *A61B 5/06* (2013.01); *A61B 5/065* (2013.01)

(58) Field of Classification Search
CPC ............ A61B 2019/5251; A61B 5/06; A61B 19/5244
See application file for complete search history.

(56) References Cited

U.S. PATENT DOCUMENTS 5,060,632 A * 10/1991 Hibino et al. ................. 600/109
5,253,647 A * 10/1993 Takahashi et al. ............ 600/424
(Continued)

FOREIGN PATENT DOCUMENTS

JP   2002-325721   11/2002
JP   2002-369790   12/2002
(Continued)

OTHER PUBLICATIONS

Extended Supplementary European Search Report dated Nov. 3, 2009.

*Primary Examiner* — Nicholas Evoy
(74) *Attorney, Agent, or Firm* — Scully, Scott, Murphy & Presser, PC

(57) ABSTRACT

A detecting apparatus includes: a change-over switch for switching on/off display of a scope model on a liquid crystal monitor; a position calculating portion for calculating respective positions of source coils; a scope model generating portion for generating a scope model of an electronic endoscope based on the respective positions of the source coils calculated by the position calculating portion; and a selector for selectively outputting to the liquid crystal monitor a display-pause-time image stored in a display-pause-time image storing portion and a scope model image from the scope model generating portion; and a control portion for controlling each of these portions. The detecting apparatus thus displays an insertion shape of the endoscope at a timing as needed.

3 Claims, 21 Drawing Sheets

(51) Int. Cl.
*A61B 1/05* (2006.01)
*A61B 5/06* (2006.01)

(56) References Cited

U.S. PATENT DOCUMENTS

| | | | | |
|---|---|---|---|---|
| 5,427,103 A * | 6/1995 | Fujio et al. | | 600/423 |
| 5,443,066 A * | 8/1995 | Dumoulin et al. | | 600/424 |
| 5,752,513 A * | 5/1998 | Acker et al. | | 600/424 |
| 5,840,024 A * | 11/1998 | Taniguchi et al. | | 600/424 |
| 5,997,473 A * | 12/1999 | Taniguchi et al. | | 600/117 |
| 6,036,637 A * | 3/2000 | Kudo | | 600/173 |
| 6,059,718 A * | 5/2000 | Taniguchi et al. | | 600/117 |
| 6,295,368 B1 * | 9/2001 | Hasegawa et al. | | 382/128 |
| 6,432,041 B1 * | 8/2002 | Taniguchi et al. | | 600/118 |
| 6,453,190 B1 * | 9/2002 | Acker et al. | | 600/424 |
| 6,468,265 B1 * | 10/2002 | Evans et al. | | 606/1 |
| 6,490,467 B1 * | 12/2002 | Bucholz et al. | | 600/407 |
| 6,511,417 B1 * | 1/2003 | Taniguchi et al. | | 600/117 |
| 6,589,163 B2 * | 7/2003 | Aizawa et al. | | 600/118 |
| 6,745,065 B2 * | 6/2004 | Niwa et al. | | 600/424 |
| 6,755,791 B2 * | 6/2004 | Kawashima | | 600/467 |
| 6,773,394 B2 * | 8/2004 | Taniguchi et al. | | 600/117 |
| 6,846,286 B2 * | 1/2005 | Suzuki et al. | | 600/145 |
| 6,868,195 B2 * | 3/2005 | Fujita | | 385/12 |
| 6,871,086 B2 * | 3/2005 | Nevo et al. | | 600/424 |
| 6,890,294 B2 * | 5/2005 | Niwa et al. | | 600/106 |
| 7,311,107 B2 * | 12/2007 | Harel et al. | | 128/899 |
| 7,706,859 B2 * | 4/2010 | Aizawa et al. | | 600/424 |
| 7,857,753 B2 * | 12/2010 | Onoda et al. | | 600/117 |
| 7,935,047 B2 * | 5/2011 | Yoshida et al. | | 600/117 |
| 8,147,404 B2 * | 4/2012 | Miyoshi et al. | | 600/145 |
| 8,192,354 B2 * | 6/2012 | Miyake et al. | | 600/117 |
| 8,211,010 B2 * | 7/2012 | Hirakawa | | 600/118 |
| 8,257,247 B2 * | 9/2012 | Oda | | 600/117 |
| 8,260,398 B2 * | 9/2012 | Uchiyama et al. | | 600/424 |
| 8,337,397 B2 * | 12/2012 | Prisco et al. | | 600/117 |
| 8,382,662 B2 * | 2/2013 | Soper et al. | | 600/182 |
| 8,412,311 B2 * | 4/2013 | Kenneth | | 600/434 |
| 8,467,615 B2 * | 6/2013 | Hirakawa | | 382/232 |
| 2002/0035321 A1 * | 3/2002 | Bucholz et al. | | 600/407 |
| 2002/0169361 A1 * | 11/2002 | Taniguchi et al. | | 600/117 |
| 2002/0183592 A1 * | 12/2002 | Suzuki et al. | | 600/145 |
| 2002/0188174 A1 * | 12/2002 | Aizawa et al. | | 600/118 |
| 2002/0198439 A1 * | 12/2002 | Mizuno | | 600/109 |
| 2003/0028094 A1 * | 2/2003 | Kumar et al. | | 600/410 |
| 2003/0028096 A1 * | 2/2003 | Niwa et al. | | 600/424 |
| 2003/0040685 A1 * | 2/2003 | Lewkowicz et al. | | 600/593 |
| 2003/0055317 A1 * | 3/2003 | Taniguchi et al. | | 600/117 |
| 2003/0055410 A1 * | 3/2003 | Evans et al. | | 606/1 |
| 2003/0187347 A1 * | 10/2003 | Nevo et al. | | 600/424 |
| 2003/0195388 A1 * | 10/2003 | Niwa et al. | | 600/117 |
| 2003/0195415 A1 * | 10/2003 | Iddan | | 600/424 |
| 2003/0199756 A1 * | 10/2003 | Kawashima | | 600/424 |
| 2004/0015075 A1 * | 1/2004 | Kimchy et al. | | 600/424 |
| 2004/0054248 A1 * | 3/2004 | Kimchy et al. | | 600/3 |
| 2004/0138552 A1 * | 7/2004 | Harel et al. | | 600/407 |
| 2004/0165810 A1 * | 8/2004 | Fujita | | 385/12 |
| 2004/0176683 A1 * | 9/2004 | Whitin et al. | | 600/424 |
| 2004/0176685 A1 * | 9/2004 | Takizawa et al. | | 600/424 |
| 2004/0204645 A1 * | 10/2004 | Saadat et al. | | 600/424 |
| 2004/0249287 A1 * | 12/2004 | Kawashima et al. | | 600/462 |
| 2005/0020879 A1 * | 1/2005 | Suzuki | | 600/118 |
| 2005/0033164 A1 * | 2/2005 | Yatsuo et al. | | 600/434 |
| 2005/0090743 A1 * | 4/2005 | Kawashima et al. | | 600/443 |
| 2005/0139222 A1 * | 6/2005 | Minai et al. | | 128/899 |
| 2005/0143642 A1 * | 6/2005 | Minai et al. | | 600/407 |
| 2005/0143643 A1 * | 6/2005 | Mimai et al. | | 600/407 |
| 2005/0143647 A1 * | 6/2005 | Minai et al. | | 600/410 |
| 2005/0143648 A1 * | 6/2005 | Minai et al. | | 600/410 |
| 2005/0171427 A1 * | 8/2005 | Nevo et al. | | 600/424 |
| 2005/0183733 A1 * | 8/2005 | Kawano et al. | | 128/899 |
| 2005/0216231 A1 * | 9/2005 | Aoki et al. | | 702/183 |
| 2005/0228221 A1 * | 10/2005 | Hirakawa | | 600/101 |
| 2006/0169293 A1 * | 8/2006 | Yokoi et al. | | 128/899 |
| 2006/0173289 A1 * | 8/2006 | Aizawa et al. | | 600/424 |
| 2007/0038063 A1 * | 2/2007 | Kuth et al. | | 600/407 |
| 2007/0049797 A1 * | 3/2007 | Yoshida et al. | | 600/117 |
| 2007/0106114 A1 * | 5/2007 | Sugimoto et al. | | 600/117 |
| 2007/0106115 A1 * | 5/2007 | Sugimoto | | 600/117 |
| 2007/0106116 A1 * | 5/2007 | Sugimoto | | 600/117 |
| 2007/0161862 A1 * | 7/2007 | Yokoi et al. | | 600/175 |

FOREIGN PATENT DOCUMENTS

| | | |
|---|---|---|
| JP | 2003-245243 | 9/2003 |
| JP | 2004-358095 | 12/2004 |
| JP | 2005-095662 | 4/2005 |

* cited by examiner

○ : SENSE COIL ORIENTED IN X AXIS
◯ : SENSE COIL ORIENTED IN Y AXIS
◯ : SENSE COIL ORIENTED IN Z AXIS

ENDOSCOPE SHAPE DETECTING APPARATUS

TECHNICAL FIELD

The present invention relates to an endoscope shape detecting apparatus for detecting the insertion shape of an endoscope by using a magnetic field generating device and a magnetic field detecting device and displays the detected shape on a display apparatus.

BACKGROUND ART

In recent years, in diagnosis using an endoscope, endoscope shape detecting apparatuses have come to be used for detecting a shape of an endoscope or the like inserted into a body or the like by using a magnetic field generating device and a magnetic field detecting device and displaying the detected shape by means of a display apparatus.

For example, Japanese Unexamined Patent Publication No. 2003-245243 and others disclose an apparatus for detecting the shape of an endoscope in insertion state by using a magnetic field and displaying the detected endoscope shape. In this apparatus, a plurality of magnetic field generating devices are driven which are disposed at predetermined intervals in an insertion portion of an endoscope to be inserted into the body to generate a magnetic field around the devices. This apparatus further detects respective three-dimensional positions of the magnetic field generating devices by means of magnetic field detecting devices disposed outside the body. The apparatus generates a curved line continually linking each of the magnetic field generating devices based on the three-dimensional positions thus detected, and displays on a display apparatus a modelled three dimensional image of the insertion portion.

By observing the image displayed on the display apparatus, an operator or the like can grasp the position of a distal end portion of the insertion portion inserted into the body and the insertion shape thereof, allowing the work of insertion to a target region or the like to be smoothly performed.

However, in the conventional endoscope shape detecting apparatus, the insertion shape of the endoscope is constantly displayed on the display apparatus. Therefore, during, for example, inspection using the endoscope image, the insertion shape image gets in the field of view in some cases even when it is not necessary to monitor the insertion shape image.

The present invention was made in view of the above-mentioned circumstances and an object thereof is to provide an endoscope shape detecting apparatus capable of displaying an insertion shape of the endoscope at a timing as needed.

DISCLOSURE OF INVENTION

An endoscope shape detecting apparatus according to one aspect of the present invention includes: a device detecting portion for, with one of a group of a plurality of magnetic field generating devices and a group of a plurality of magnetic field detecting devices being disposed inside an insertion portion of an endoscope to be inserted into a subject and the other of the groups of devices being disposed outside the subject, detecting respective positions of the one group of devices disposed inside the insertion portion by using positions of the other group of devices as reference; a shape estimating portion for controlling the device detecting portion and estimating a shape of the endoscope insertion portion based on a detection result of the device detecting portion; a model image generating portion for generating a model image of the shape of the endoscope insertion portion estimated by the shape estimating portion; and an image display controlling portion for controlling display of the model image on a display portion.

BEST MODE FOR CARRYING OUT THE INVENTION

Figure 1:
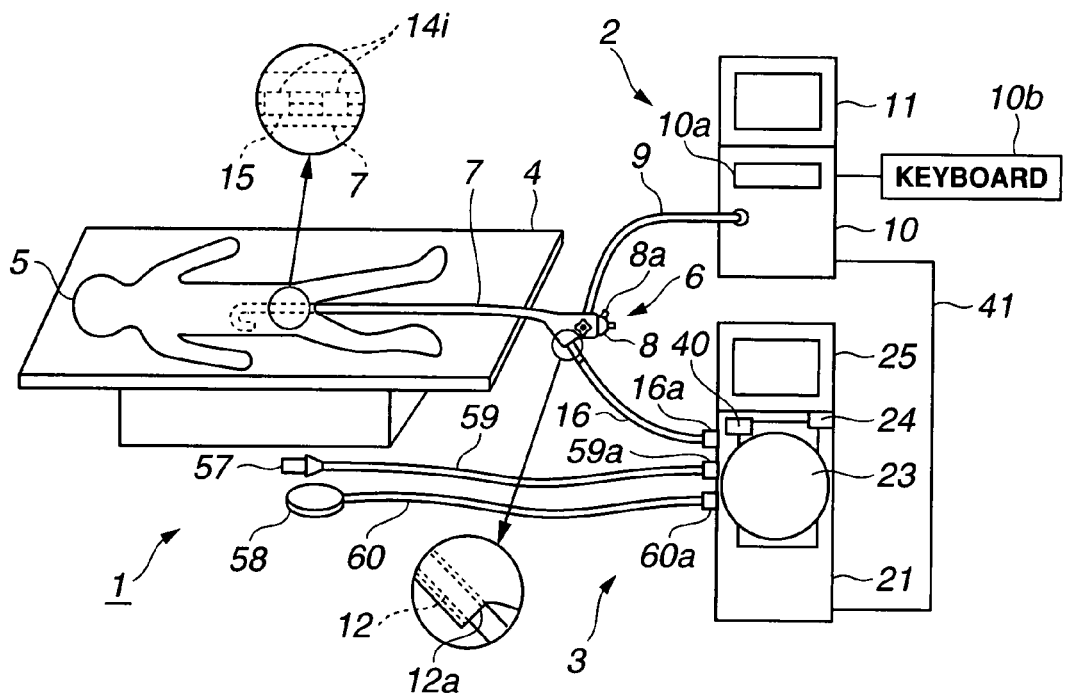
FIG. 1 is a configuration diagram showing a configuration of an endoscope system according to a first embodiment of the present invention.

Referring to the drawings, embodiments of the present invention are described below.

First Embodiment

FIGS. 1 to 12 show a first embodiment of the present invention.

As shown in FIG. 1, an endoscope system 1 of the present embodiment includes an endoscope apparatus 2 for performing endoscopy and an endoscope shape detecting apparatus 3 used to assist the endoscopy. The endoscope shape detecting apparatus 3 is used as an insertion assisting apparatus when an operator performs endoscopy with an electronic endoscope 6. In other words, the operator carries out insertion of an insertion portion 7 of the electronic endoscope 6 into a body cavity of a patient 5 lying on a bed 4, receiving insertion assistance by the endoscope shape detecting apparatus 3.

The electronic endoscope 6 includes an elongate insertion portion 7 having flexibility and provided on a distal end portion side with a bending portion, and an operation portion 8 at a rear end of the insertion portion 7, provided with a bending operation portion for operating to bend the bending portion. The operation portion 8 has a universal cord 9 extending from a side portion thereof and connected to a video processor 10. The video processor 10 is provided on a front surface with a panel switch 10a. The video processor 10 can be connected with a keyboard 10b.

The electronic endoscope 6 includes a light guide disposed and inserted therein. The electronic endoscope 6 is designed to transmit illumination light from a light source portion in the video processor 10 to a distal end side of the insertion portion 7, via the light guide. The electronic endoscope 6 emits the illumination light transmitted via the light guide, from an illumination window provided at the distal end of the insertion portion 7, so as to illuminate the subject (object). Reflected light from the subject (object) is formed into a subject image by an object lens disposed on a backward side of an observation window provided in the distal end portion of the insertion portion 7. At image formation position of the object lens, an image pickup device (CCD) is disposed to photoelectrically convert a subject image. Note that the observation window is provided adjacent to the illumination window.

Signals photoelectrically converted by the image pickup device (CCD) are subjected to signal processing by a video signal processing portion in the video processor 10. The video signal processing portion in the video processor 10 then generates a standard video signal to display a subject (object) image on an image observation monitor 11 connected to the video processor 10.

The electronic endoscope 6 has a forceps channel 12, into which a probe 15 can be inserted from a channel insertion port 12a. The probe 15 includes along an insertion axis, for example 16 magnetic field generating devices (or source coils) 14a, 14b . . . , 14p (hereinafter represented by symbol 14i). Thus, the electronic endoscope 6 is configured so that inserting the probe 15 into the forceps channel 12 results in the source coils 14i being set in the insertion portion 7.

The probe 15 includes a source cable 16 extending from rear end thereof which serves as a drive signal transferring portion. The source cable 16 has at a rear end thereof a connector 16a which is detachably connected to a detecting apparatus (also denominated as an apparatus main body) 21 as an apparatus main body of the endoscope shape detecting apparatus 3. By the detecting apparatus 21 applying via the source cable 16 a drive signal to the source coils 14i serving as magnetic field generating portions, the source coils 14i generate a magnetic field.

Furthermore, the detecting apparatus 21 is disposed near a bed 4 on which the patient 5 lies. The detecting apparatus 21 is provided with a (sensing) coil unit 23 in a manner freely movable (ascendable/descendable) in up/down direction on the vertical axis with respect to the bed 4. In the coil unit 23, a plurality of magnetic field detecting devices (sensing coils) are disposed.

Figure 2:
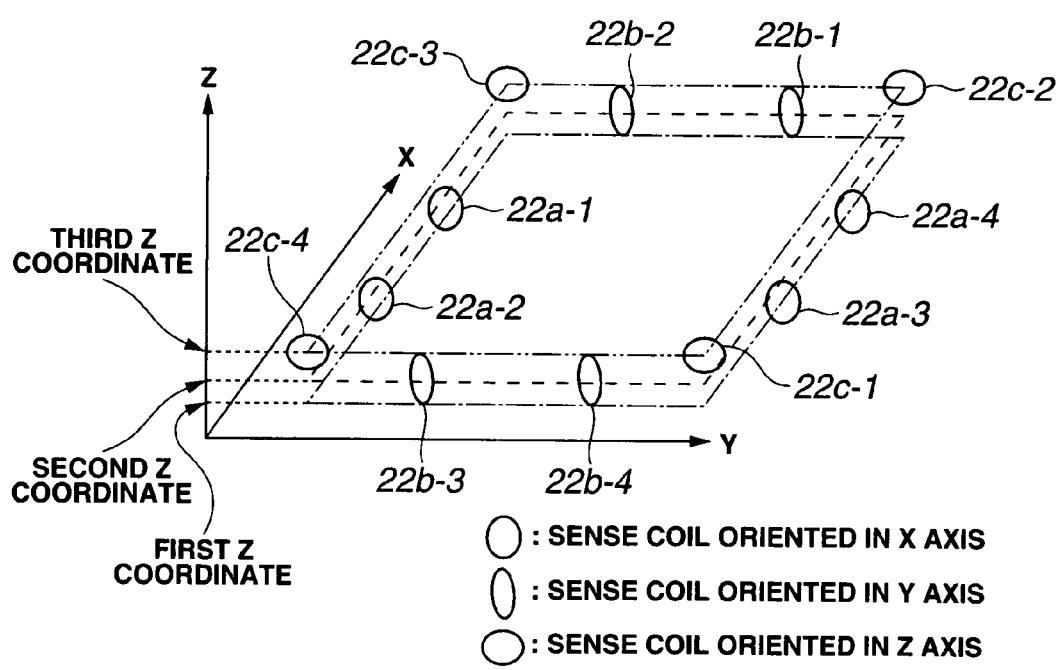
FIG. 2 is a view showing an exemplary disposition of coils incorporated in a coil unit of FIG. 1.

To describe more specifically, the coil unit 23 is configured by disposing, for example, 12 sensing coils (hereinafter represented by symbol 22j) as shown in FIG. 2: sensing coils 22a-1, 22a-2, 22a-3, 22a-4 having centers whose Z-coordinate is a first Z-coordinate and (having coil surfaces whose normal vectors are) oriented in X-axis, for example; sensing coils 22b-1, 22b-2, 22b-3, 22b-4 having centers whose Z-coordinate is a second Z-coordinate different from the first Z-coordinate and (having coil surfaces whose normal vectors are) oriented in Y-axis; and sensing coils 22c-1, 22c-2, 22c-3, 22c-4 having centers whose Z-coordinate is a third Z-coordinate different from the first and second Z-coordinates and (having coil surfaces whose normal vectors are) oriented in Z-axis.

The sensing coils 22j are connected to the detecting apparatus 21 via a cable not shown from the coil unit 23. The detecting apparatus 21 is provided with an operation panel 24 for apparatus operation by a user. On an upper part of the detecting apparatus 21, there is disposed a liquid crystal monitor 25 as a display portion to display the detected shape of the endoscope insertion portion (hereinafter denoted as a scope model).

In the present embodiment, the detecting apparatus 21 can be connected and used with an out-of-body marker 57 and a reference plate 58 for checking the position of the insertion portion 7 inserted into the body, as shown in FIG. 1.

The reference plate 58 is, for example, attached on the abdomen of the patient 5, and connected to the detecting apparatus 21. The reference plate 58 can be used for a purpose such as constantly displaying a scope model from a specific direction (of the patient 5) even when the body position of the patient 5 changes.

Specifically, the out-of-body marker 57 accommodates therein a single source coil, and is provided with a cable 59 having at a proximal end thereof a connector 59a detachably connected to the detecting apparatus 21.

By connecting the connector 59a to the detecting apparatus 21, the out-of-body marker 57 drives the source coil of the out-of-body marker 57 as in the case of the source coil 14i in the probe 15. The detecting apparatus 21 also displays, like the scope model, position of the source coil of the out-of-body marker 57 detected by the coil unit 23, on the liquid crystal monitor 25.

The reference plate 58 includes, for example, three source coils disposed inside a disk-shaped portion of the plate. These three source coils are connected with a cable 60, which is provided at a proximal end thereof with a connector 60a that is detachably connected to the detecting apparatus 21. The detecting apparatus 21 can thus detect positions of the three source coils of the reference plate 58 at the coil unit 23.

By detecting the positions of the exemplary three source coils of the reference plate 58, the detecting apparatus 21 determines a surface of the reference plate 58 on which the three source coils are disposed. The detecting apparatus 21 then uses the determined surface of the reference plate 58 to draw the scope model as is observed when the insertion portion 7 is viewed from a direction perpendicular to the surface of the reference plate 58.

The detecting apparatus 21 and the video processor 10 are connected by a signal cable 41, via which various kinds of data can be transmitted and received between the detecting apparatus 21 and the video processor 10.

Figure 3:
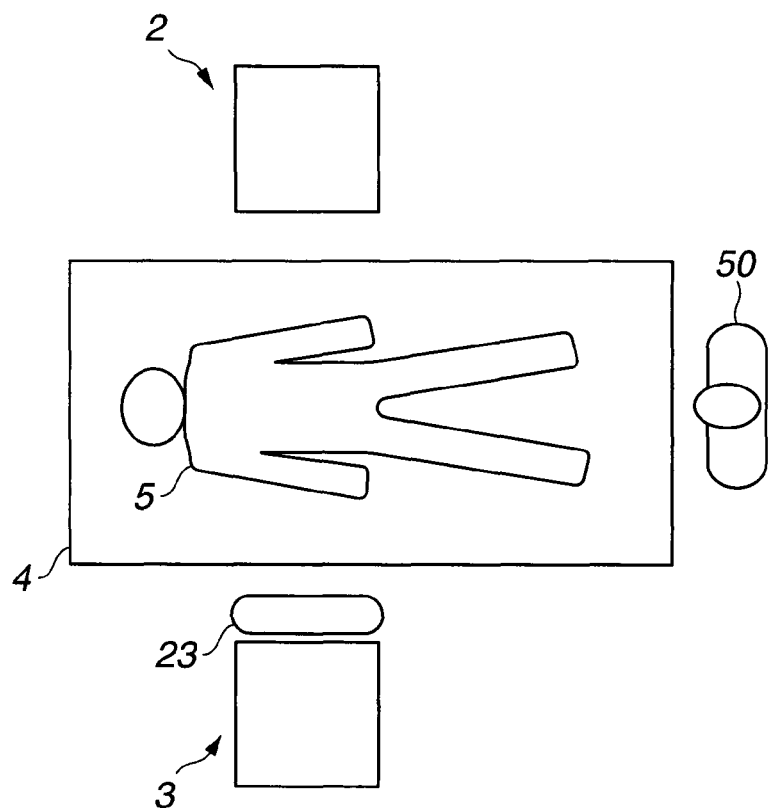
FIG. 3 is a first view showing an exemplary disposition of an endoscope apparatus and an endoscope shape detecting apparatus of FIG. 1.
Figure 4:
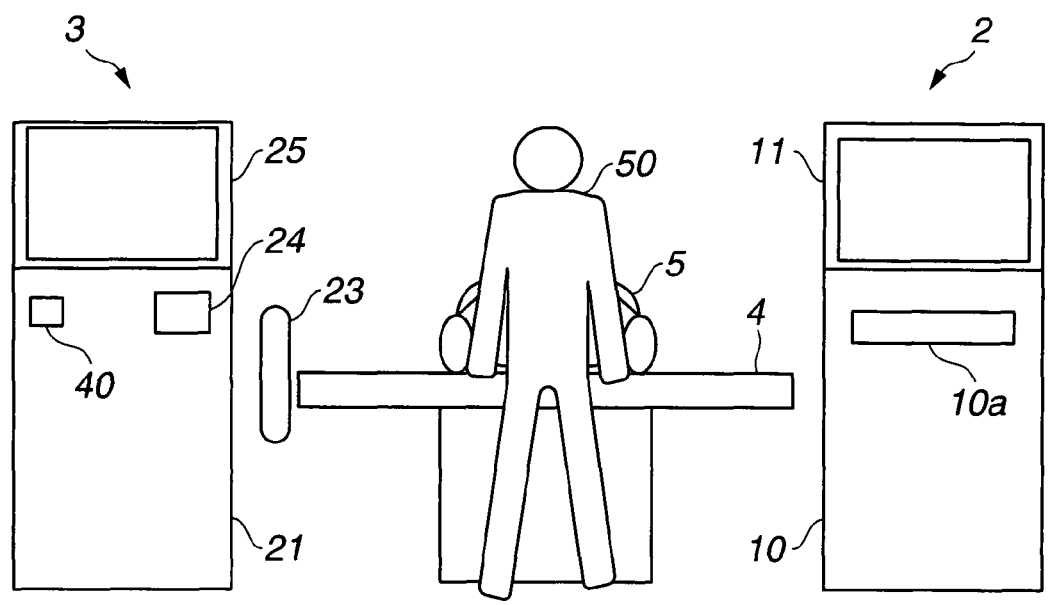
FIG. 4 is a second view showing an exemplary disposition of the endoscope apparatus and the endoscope shape detecting apparatus of FIG. 1.

FIGS. 3 and 4 show an exemplary disposition of the endoscope apparatus 2 and the endoscope shape detecting apparatus 3 with respect to the patient 5 and the operator 50. As shown in the drawings, the endoscope apparatus 2 and the endoscope shape detecting apparatus 3 are disposed in a state sandwiching the patient 5, such that display screens of the monitor 11 of the endoscope apparatus 2 and the liquid crystal monitor 25 of the endoscope shape detecting apparatus 3 are directed to the operator 50.

On the liquid crystal monitor 25 and the monitor 11 thus disposed (in the manner mentioned above and shown in FIGS. 3 and 4), the operator 50 can observe an endoscope shape image during insertion (scope model) by the liquid crystal monitor 25 mainly in an insertion procedure, and an endoscope image by the monitor 11 mainly in observing and treating a diseased part.

Figure 5:
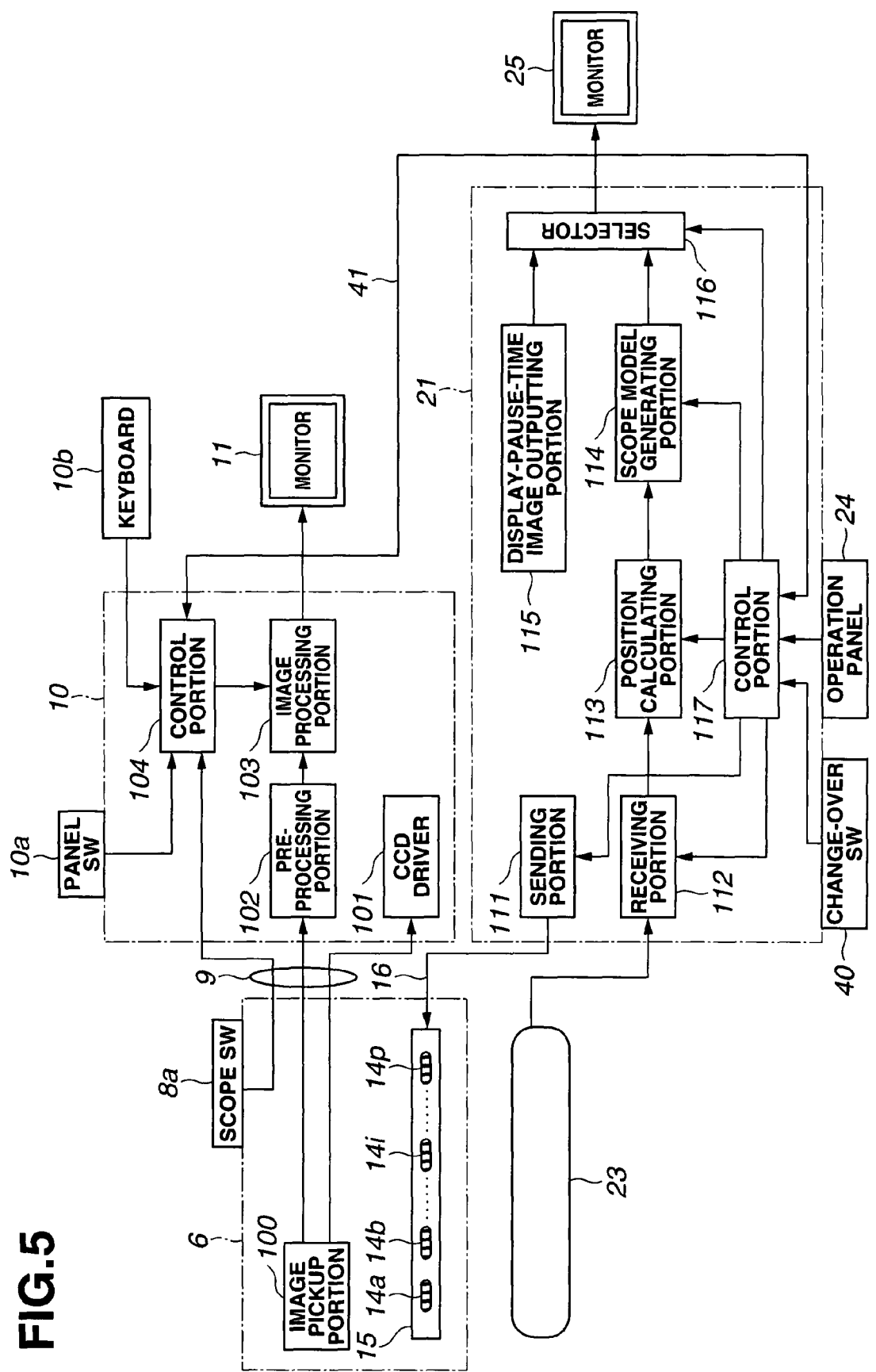
FIG. 5 is a block diagram showing a configuration of a video processor and a detecting apparatus of FIG. 1.

As shown in FIG. 5, the detecting apparatus 21 includes a sending portion 111, a receiving portion 112, a position calculating portion 113 as a device detecting portion, a scope model generating portion 114 as a model image generating portion, a display-pause-time image storing portion 115, a selector 116, and a control portion 117 as a shape estimating portion for controlling each of these portions.

The sending portion 111 is for driving the exemplary 16 source coils 14i disposed in the probe 15. The receiving portion 112 is for receiving detection signals from the sensing coils 22j in the (sensing) coil unit 23.

The position calculating portion 113 calculates respective positions of the source coils 14i based on the detection signals from the sensing coil 22j received by the receiving portion 112. The scope model generating portion 114 generates a scope model of the electronic endoscope 6 based on the respective positions of the source coils 14i calculated by the position calculating portion 113.

The selector 116 selectively outputs on the liquid crystal monitor 25 a display-pause-time image stored in the display-pause-time image storing portion 115 and a scope model image from the scope model generating portion 114.

The control portion 117 reads the operation panel 24 and a change-over switch 40 of the detecting apparatus 21 at a predetermined timing to accept an instruction/setting therefrom. Note that, by operating the change-over switch 40, the selector 116 is controlled by the control portion 117.

Furthermore, the display-pause-time image stored in the display-pause-time image storing portion 115 is an image in, for example, black or gray all over.

For example, in some cases, an operator skilled in insertion procedure may continue insertion, observing the endoscope image even in insertion procedure. However, in such insertion procedure observing an endoscope image and in endoscope observation after the insertion procedure, displaying a scope model on the liquid crystal monitor 25 may result in the scope model on the liquid crystal monitor 25 getting in the observation field of view of the operator of the endoscope image of monitor 11 even when it is unnecessary to view the insertion shape image. Here, merely stopping the scope model generating portion 114 from generating the scope model and outputting an image signal without the image of the scope model from the scope model generating portion 114 from the selector 116 to the liquid crystal monitor 25 may in some cases cause distortion of the display image on the liquid crystal monitor 25 or noise to be displayed on the image.

Accordingly, in the present embodiment, the display-pause image outputting portion 115 is complementarily provided in order to prevent distortion of the displaying image on the liquid crystal monitor 25 and noise from being displayed thereon when stopping displaying the image of the scope model generating portion 114 on the liquid crystal monitor 25. That is, when it is unnecessary to view the insertion shape image, the control portion 117 controls the selector 116 to display the display-pause-time image stored in the display-pause-time image storing portion 115 on the liquid crystal monitor 25, as mentioned above.

Note that, instead of providing the display-pause image outputting portion 115, the selector 116 may be used as a switch such that the control portion 117 controls the selector 116 to switch on/off the output signal of the scope model from the scope model generating portion 114 with respect to the monitor 11.

To that end, in the present embodiment, the detecting apparatus 21 includes the change-over switch 40 as an image display controlling portion (see FIGS. 1 and 4) for controlling to switch on/off the display of the scope model on the liquid crystal monitor 25 (for example, for controlling to display whether an image from the scope model generating portion 114 or a display-pause-time image stored in the display-pause-time image storing portion 115).

As shown in FIG. 5, the video processor 10 includes a CCD driver 101, a preprocessing portion 102, an image processing portion 103, and a control portion 104. The CCD driver 101 is for driving an image pickup device, e.g., a CCD, of the image pickup portion 100 provided in a distal end of the electronic endoscope 6. The preprocessing portion 102 performs a processing such as correlative double sampling with respect to an image pickup signal from the image pickup portion 100. The image processing portion 103 performs image processings such as, for example, RGB matrix processing, outline emphasis processing, and color correction processing with respect to a signal from the preprocessing portion 102. The control portion 104 controls each of these portions of the video processor 10.

The control portion 104 reads, at a predetermined timing, input from input portions such as a scope switch 8a provided to the operation portion 8 (see FIG. 1) of the electronic endoscope 6 and the panel switch 10a and the keyboard 10b of the video processor 10, to accept instructions/settings from these input portions. An image processed by the image processing portion 103 is outputted to the monitor 11, so that an endoscope image can be observed on the monitor 11.

Actions of the present embodiment thus configured are described.

Figure 6:
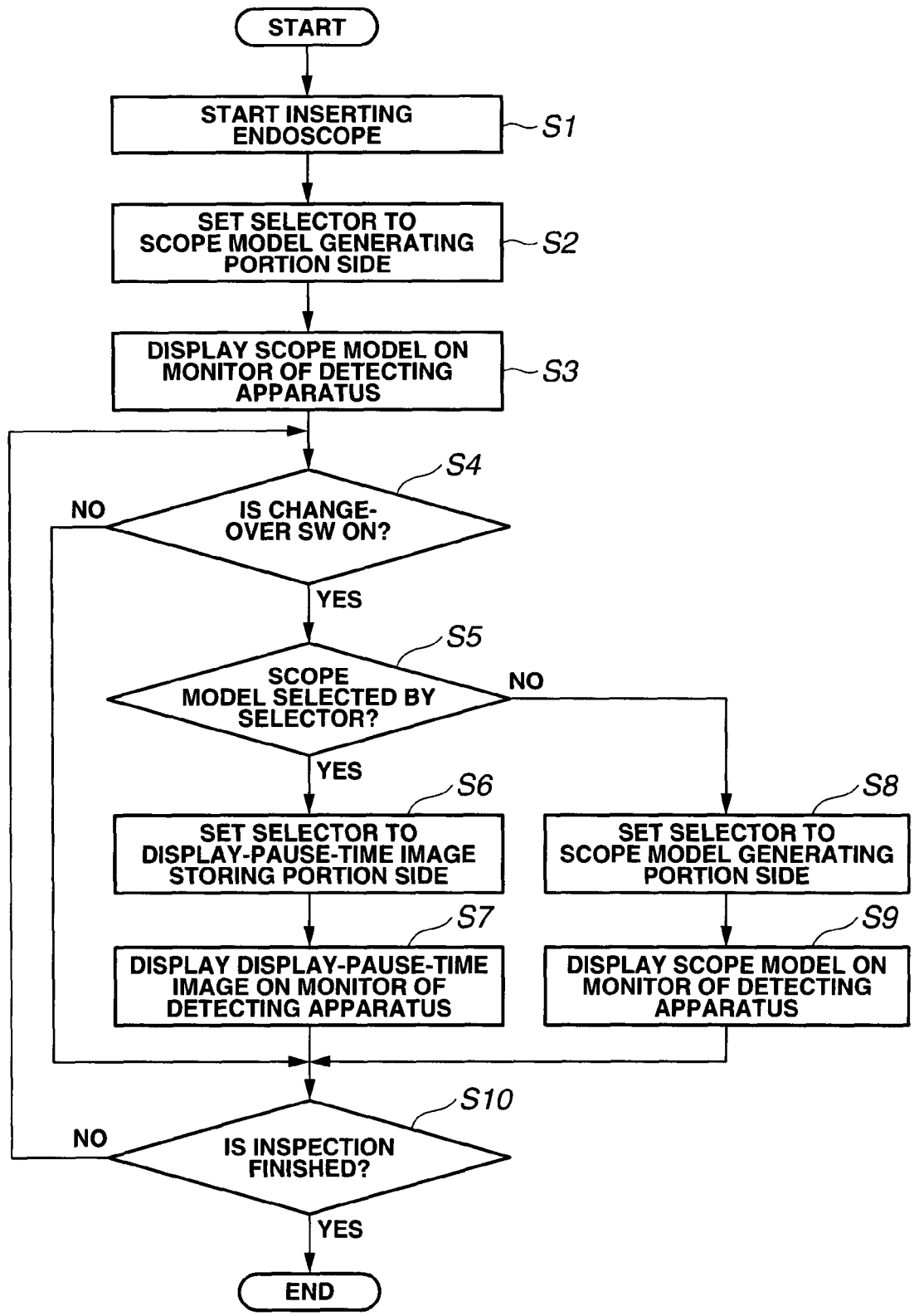
FIG. 6 is a flow chart illustrating actions of the detecting apparatus of FIG. 5.

As shown in FIG. 6, when insertion of the electronic endoscope 6 is started in step S1, the control portion 117 sets the selector 116 to the scope model generating portion 114 side in step S2. This causes the control portion 117 to display a scope model as an image from the scope model generating portion 114 on the liquid crystal monitor 25 via the selector 116 in step S3.

Figure 7:
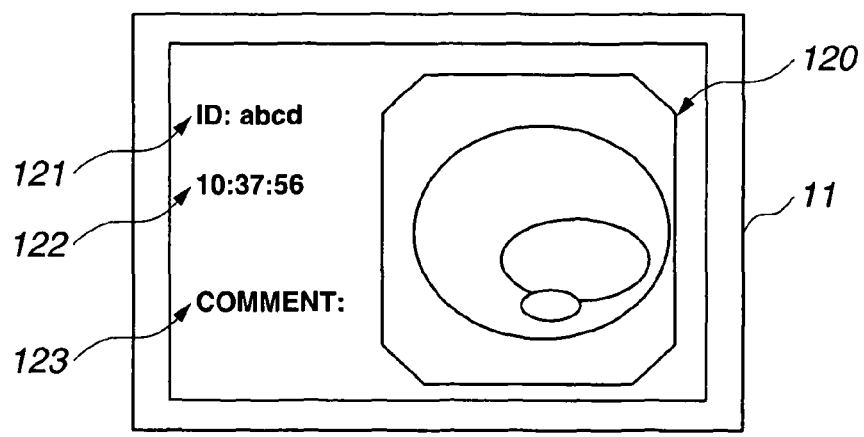
FIG. 7 is a first view illustrating processing of FIG. 6.

At this time, the monitor 11 displays an endoscope image 120 from the electronic endoscope 6 as shown in FIG. 7, and the liquid crystal monitor 25 displays a scope model 130 as mentioned above as shown in FIG. 8. The display image of the monitor 11 includes, near the display area of the endoscope image 120 on the screen, display areas for displaying various data such as a patient ID display area 121, a time information display area 122, and a comment display area 123. Also, the display image of the liquid crystal monitor 25 includes, near the display area of the scope model 130 on the screen, display areas for displaying various data such as a patient ID display area 131 and a time information display area 132.

Figure 8:
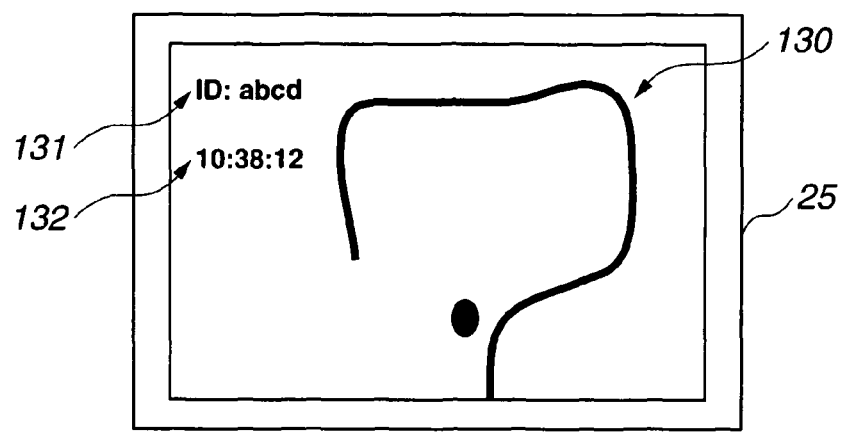
FIG. 8 is a second view illustrating processing of FIG. 6.

In the present embodiment, the video processor 10 and the detecting apparatus 21, which have configurations independent from each other, may in some cases have different pieces of time information, respectively. In such a case, different pieces of time information are displayed respectively on the time information display area 122 on the monitor 11 and the time information display area 132 on the liquid crystal monitor 25 as shown in FIGS. 7 and 8.

Figure 9:
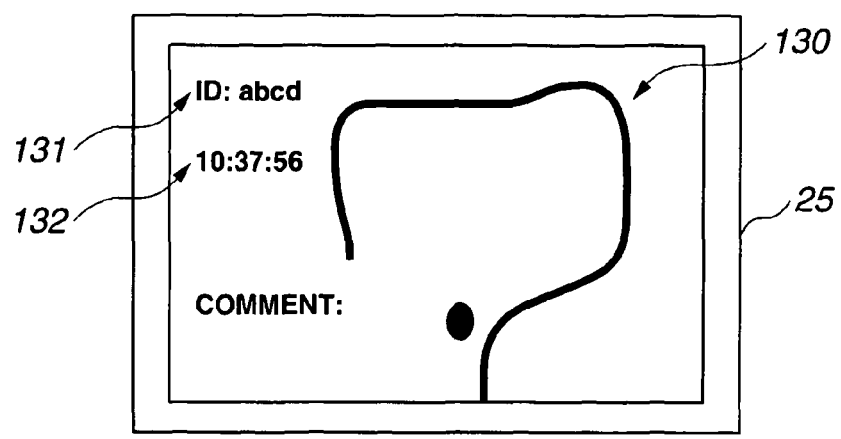
FIG. 9 is a third view illustrating processing of FIG. 6.

In the present embodiment, the control portion 104 of the video processor 10 and the control portion 117 of the detecting apparatus 21 are connected by the signal cable 41. In the present embodiment, for example, the control portion 117 of the detecting apparatus 21 reads time information of the video processor 10 by means of the signal cable 41 to calibrate time information of the detecting apparatus 21. Though this calibration, the control portion 117 matches the time information displayed in the time information display area 132 of the liquid crystal monitor 25 with the time information displayed in the time information display area 122 of the monitor 11 shown in FIG. 7, as shown in FIG. 9. Note that the control portion 117 calibrates not only the time information but also information such as a patient ID and comment.

Then, in step S4, the control portion 117 judges whether or not the change-over switch 40 is turned on. If the change-over switch 40 is turned on, the control portion 117 judges, in step S5, the state of the selector 116 as to whether or not the scope model is selected. If the scope model is selected by the selector 116, the process proceeds to step S6. If the display-pause-time image is selected by the selector 116, the process proceeds to step S8.

In step S6, the control portion 117 sets the selector 116 to the display-pause-time image storing portion 115 side, and in step S7, displays the display-pause-time image on the liquid crystal monitor 25. The process then proceeds to step S10.

Meanwhile, in step S8, the control portion 117 sets the selector 116 to the scope model generating portion 114 side, and in step S9, displays a scope model on the liquid crystal monitor 25. The process then proceeds to step S10.

Figure 10:
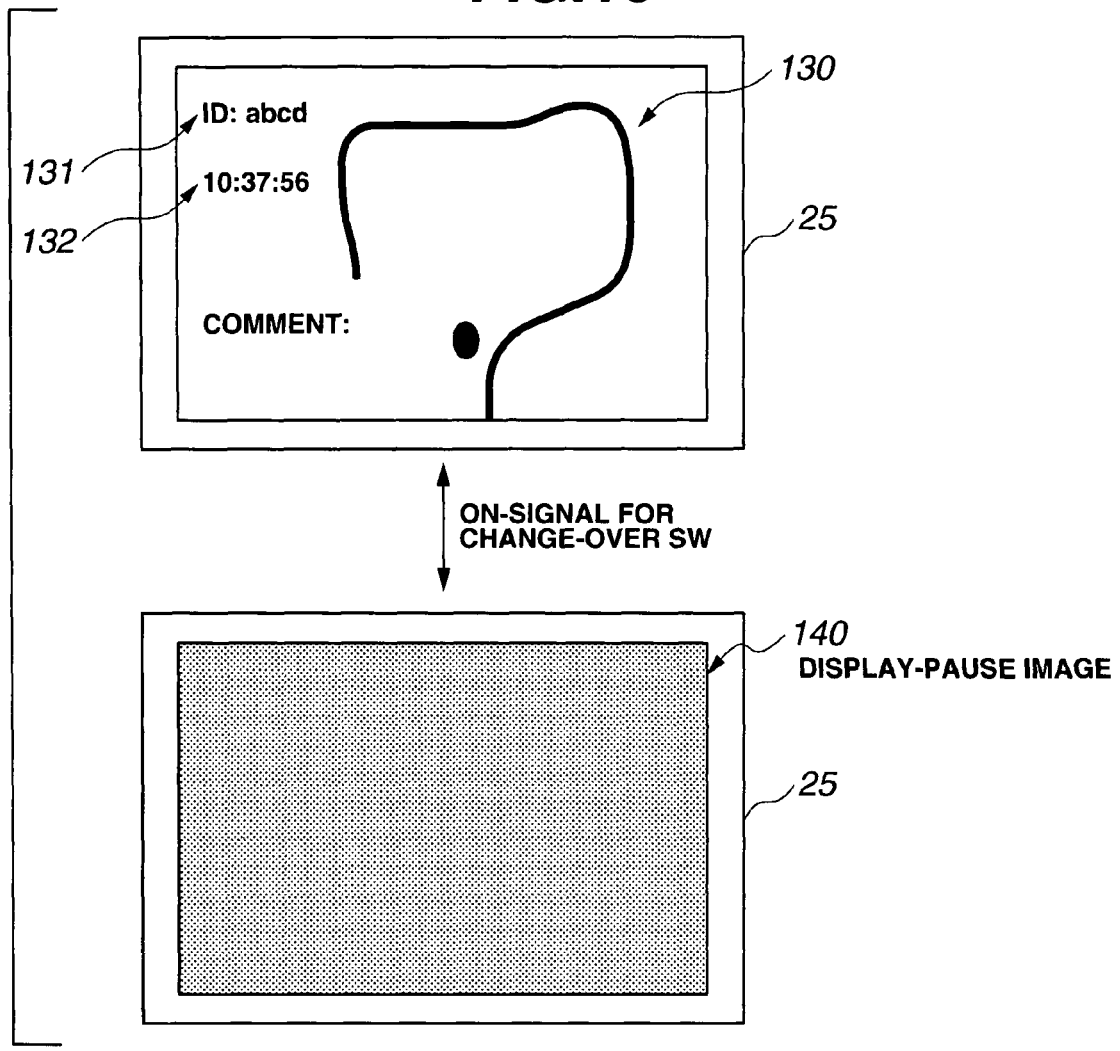
FIG. 10 is a fourth view illustrating processing of FIG. 6.
Figure 11:
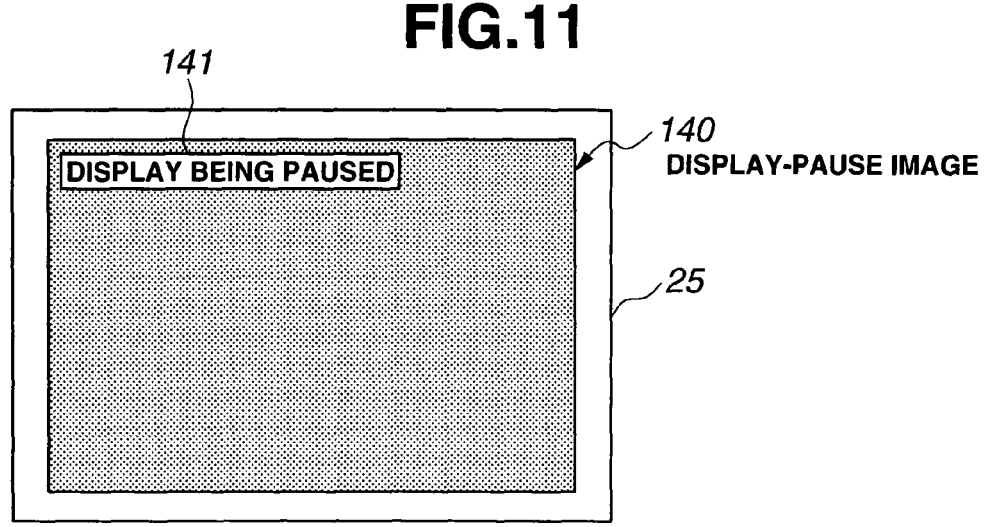
FIG. 11 is a fifth view illustrating processing of FIG. 6.

Through the processing of the steps S5 to S9, the control portion 117 performs control to display an image on the liquid crystal monitor 25 in a toggling manner while changing over between the scope model 130 and the display-pause-time image 140 by an ON signal from the change-over switch 40, as shown in FIG. 10. Note that, character information 141 indicative of a display-pause-time image may be superposedly displayed on the display-pause-time image 140 as shown in FIG. 11.

The control portion 117 then repeats the processings of the above steps S4 to S9 until the inspection is finished in step S10.

Thus, in the present embodiment, the detecting apparatus 21 is provided with the change-over switch 40 for switching on/off the display of the scope model on the liquid crystal monitor 25, so that the insertion shape of the endoscope can be displayed at a timing as needed by operating the change-over switch 40.

Figure 12:
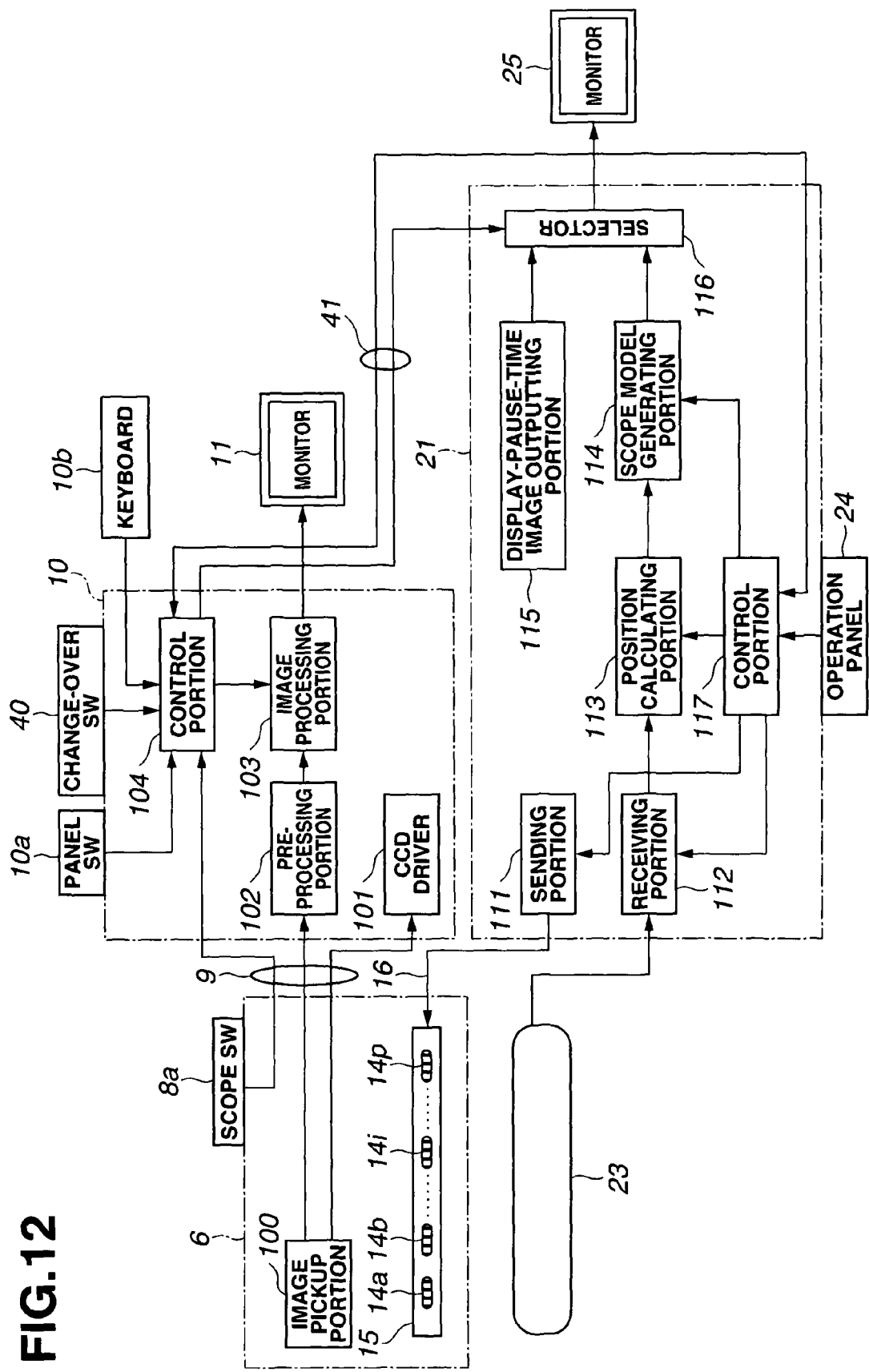
FIG. 12 is a block diagram showing a configuration of a modification example of the video processor and the detecting apparatus of FIG. 5.

Note that, although the change-over switch 40 is assumed to be provided to the detecting apparatus 21, no limitation is placed thereon. The change-over switch 40 may be provided to the video processor 10 such that the control portion 104 of the video processor 10 switches over the selector 116 via the signal cable 41, as shown in FIG. 12.

Furthermore, in place of the change-over switch 40, the switching function thereof may be allocated to the operation panel 24, the panel switch 10a, the scope switch 8a, or the keyboard 10b, such that the selector 116 is switched over by operating the operation panel 24, the panel switch 10a, the scope switch 8a, or the keyboard 10b.

Second Embodiment

FIGS. 13 to 20 show a second embodiment of the present invention.

Because the second embodiment is almost the same as the first embodiment, only different points are described. The same components are attached with the same symbols, omitting descriptions thereof.

Figure 13:
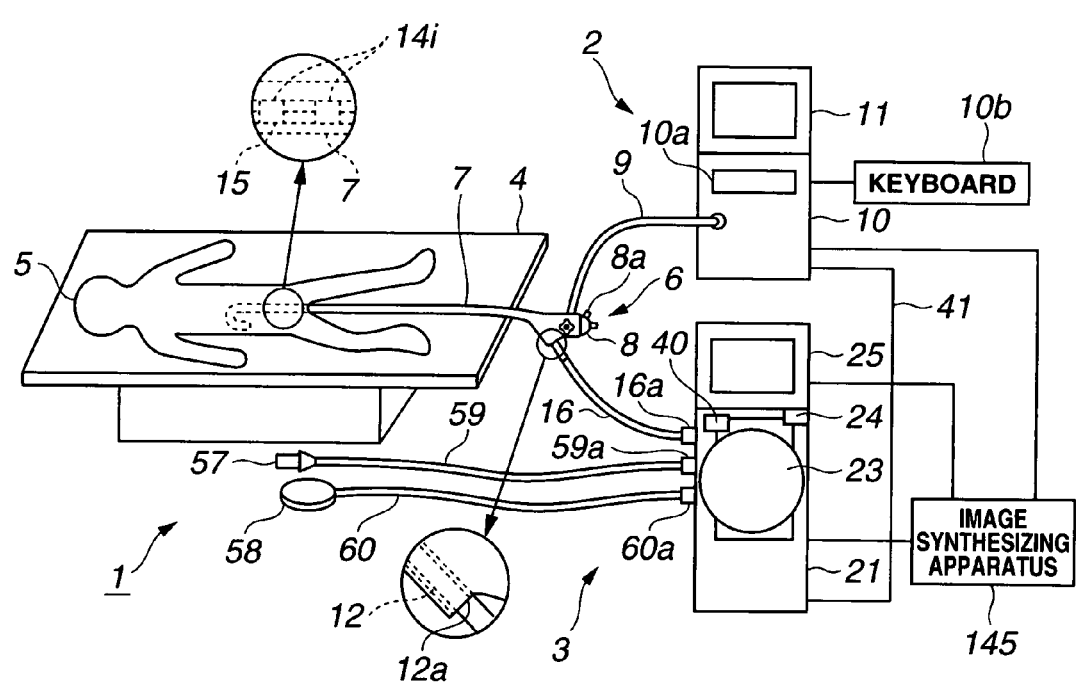
FIG. 13 is a configuration diagram showing a configuration of an endoscope system according to a second embodiment of the present invention.

As shown in FIG. 13, the present embodiment includes an image synthesizing apparatus 145 for synthesizing an endoscope image from the video processor 10 and an scope model image from the detecting apparatus 21 and displaying the synthesized image on the liquid crystal monitor 25.

Figure 14:
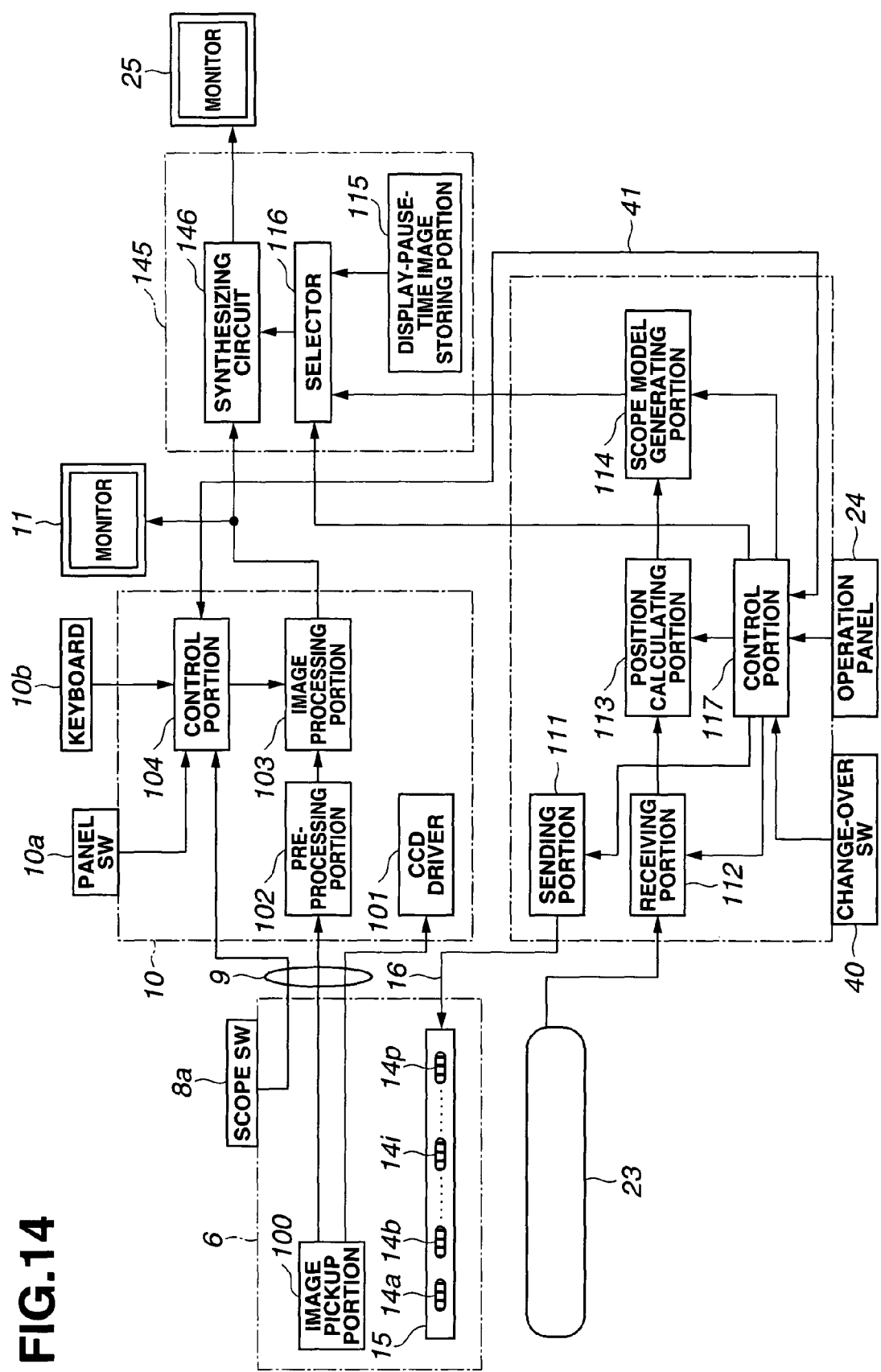
FIG. 14 is a block diagram showing a configuration of a video processor and a detecting apparatus of FIG. 13.
Figure 15:
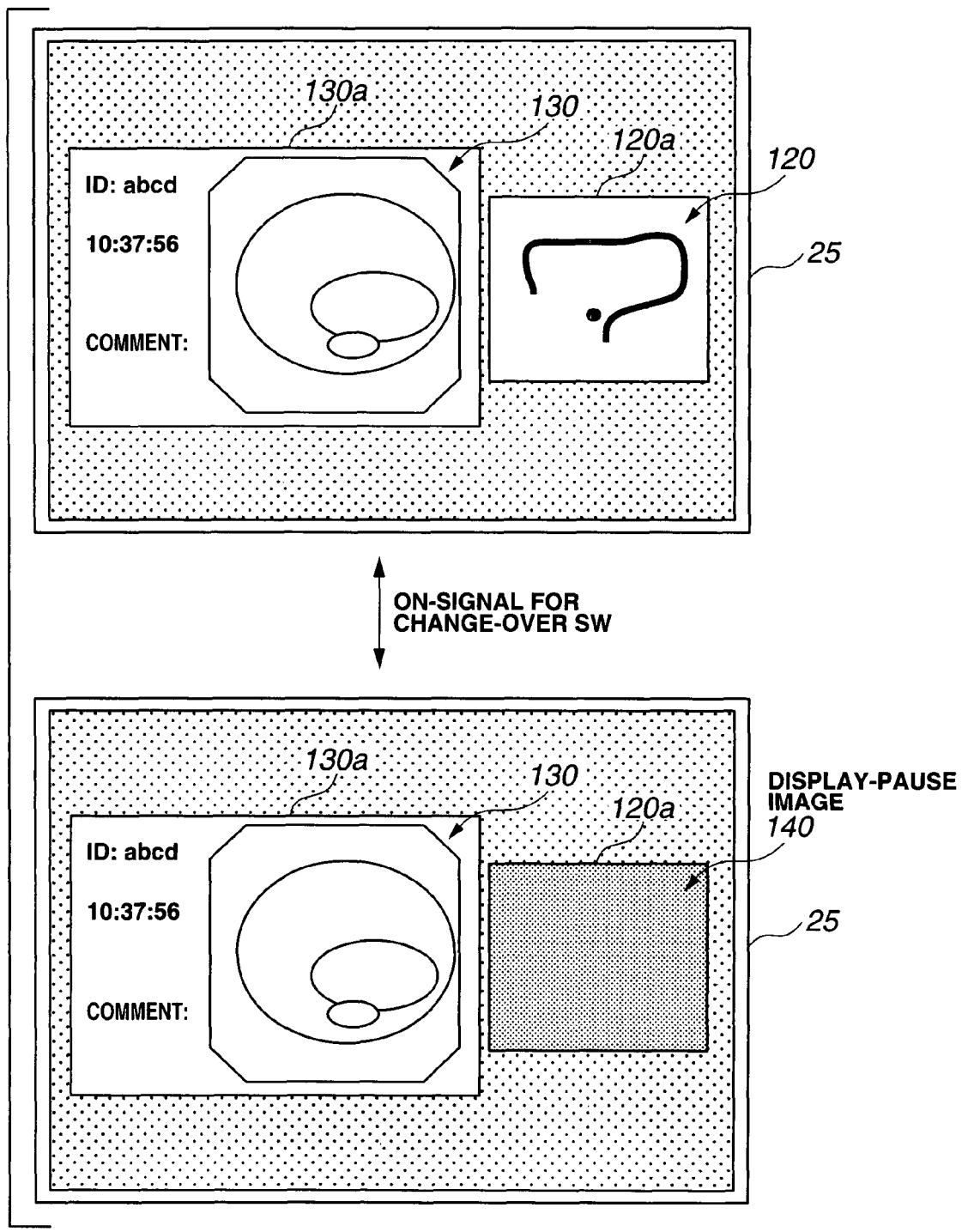
FIG. 15 is a first view illustrating actions of the detecting apparatus of FIG. 14.

As shown in FIG. 14, the image synthesizing apparatus 145 includes the display-pause-time image storing portion 115, the selector 116, and a synthesizing circuit 146. The selector 116 selectively outputs to the synthesizing circuit 146 a display-pause-time image and a scope model image from the scope model generating portion 114 of the detecting apparatus 21. The synthesizing circuit 146 is inputted with an endoscope image from the image processing portion 103 of the video processor 10, and synthesizes the endoscope image and the scope model image (or the display-pause-time image) to display a synthesized image as shown in FIG. 15 on the liquid crystal monitor 25.

The synthesized image displayed on the liquid crystal monitor 25 is configured from an endoscope image display area 130a for displaying the endoscope image 130 and a shape display area 120a for displaying the scope model image 120.

Figure 16:
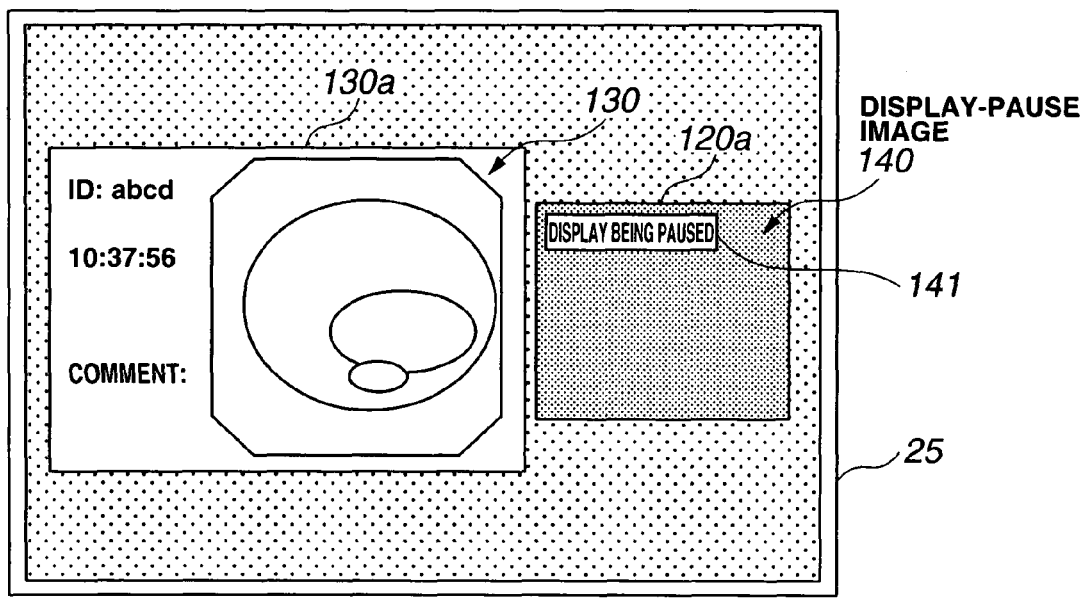
FIG. 16 is a second view illustrating actions of the detecting apparatus of FIG. 14.

The selector 116 is controlled by the control portion 117 of the detecting apparatus 21 based on an ON signal from the change-over switch 40 provided to the detecting apparatus 21. As shown in FIG. 15, the control portion 117 performs control to display an image in the shape display area 120a of the liquid crystal monitor 25 in a toggling manner while changing over between the scope model 130 and the display-pause-time image 140. Note that, character information 141 indicative of the display-pause-time image may be superposedly displayed on the display-pause-time image 140 in the shape display area 120a, as shown in FIG. 16.

Thus, in the present embodiment, the insertion shape of the endoscope can be displayed at a timing as needed by operating the change-over switch 40, as in the first example.

Figure 17:
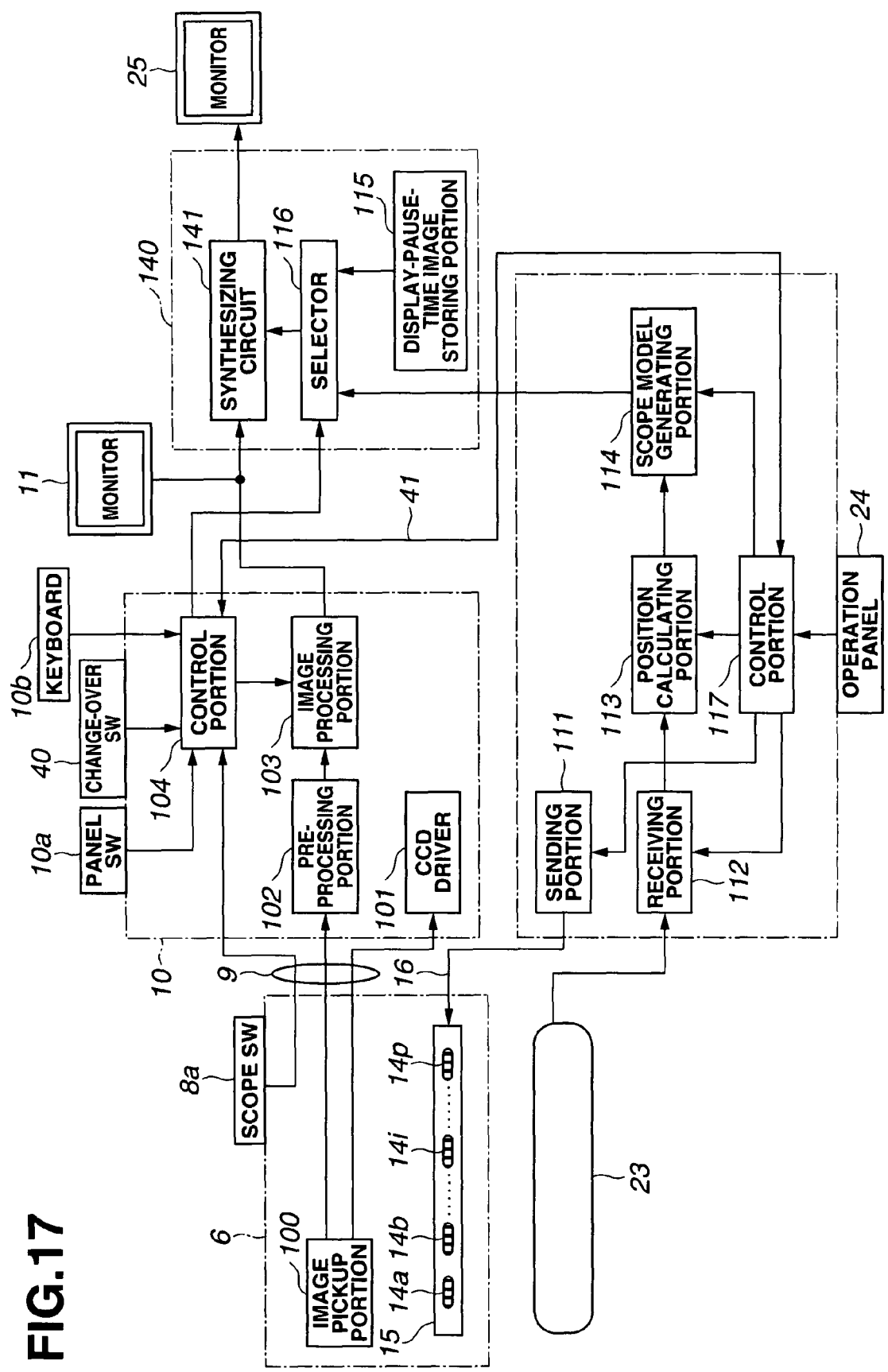
FIG. 17 is a block diagram showing a configuration of a first modification example of the video processor and the detecting apparatus of FIG. 14.

Note that, although the change-over switch 40 is assumed to be provided to the detecting apparatus 21, no limitation is placed thereon. The change-over switch 40 may be provided to the video processor 10 such that the control portion 104 of the video processor 10 switches over the selector 116 via the signal cable 41, as shown in FIG. 17.

Furthermore, in place of the change-over switch 40, the switching function thereof may be allocated to the operation panel 24, the panel switch 10a, the scope switch 8a, or the keyboard 10b, so that the selector 116 is switched over by operating the operation panel 24, the panel switch 10a, the scope switch 8a, or the keyboard 10b.

Figure 18:
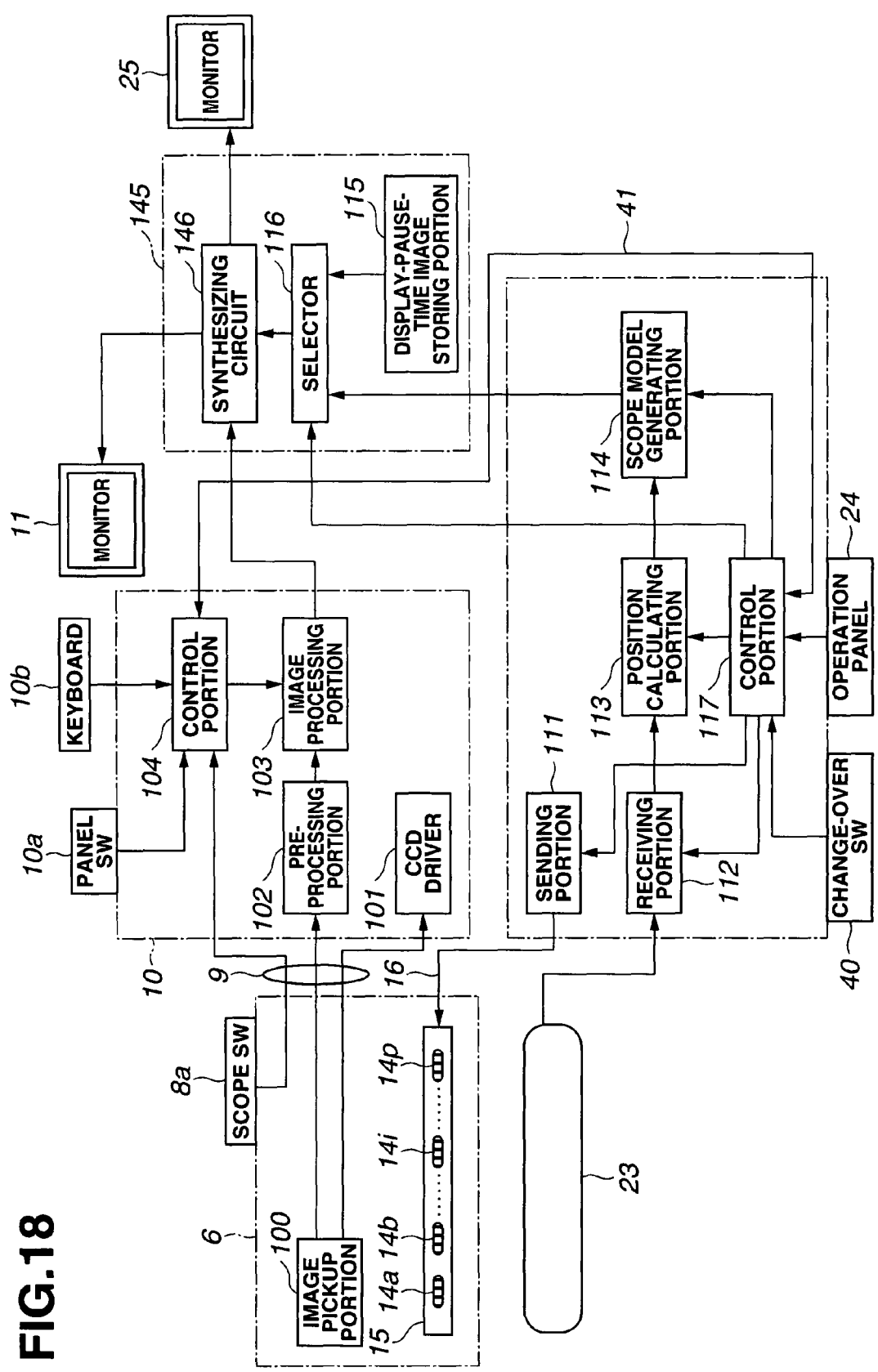
FIG. 18 is a block diagram showing a configuration of a second modification example of the video processor and the detecting apparatus of FIG. 14.

Furthermore, as shown in FIG. 18, the synthesizing circuit 146 of the image synthesizing apparatus 145 may generate two synthesized images, which is outputted respectively to the monitor 11 and the liquid crystal monitor 25.

Figure 19:
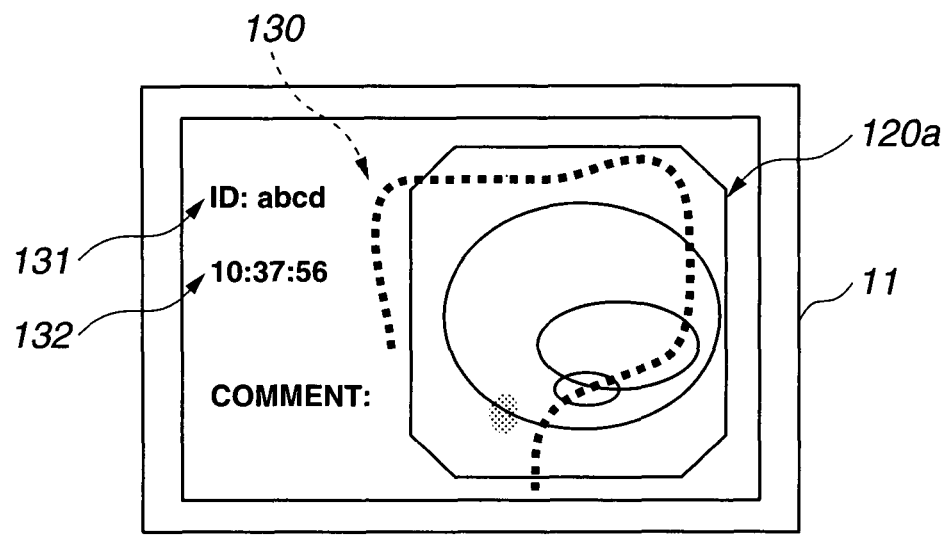
FIG. 19 is a first view illustrating actions of the detecting apparatus of FIG. 18.

That is, with respect to the monitor 11, the synthesizing circuit 146 outputs, for example, a synthesized image in which the endoscope image 120 is superposed with the scope model image 130 provided as a semitransparent image, as shown in FIG. 19.

Figure 20:
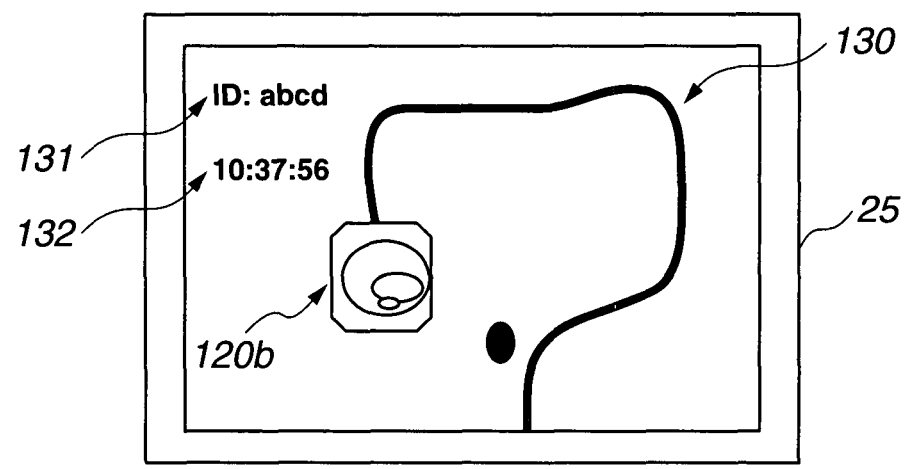
FIG. 20 is a second view illustrating actions of the detecting apparatus of FIG. 18.

Meanwhile, with respect to the liquid crystal monitor 25, the synthesizing circuit 146 for example outputs a synthesized image in which the scope model image 130 is superposed at a distal end position thereof with a reduced image 120b of the endoscope image that changes following the movement of the distal end, as shown in FIG. 20. The reduced image of the endoscope image may be substituted by a cut-out image of the endoscope image.

Third Embodiment

FIGS. 21 to 24 show a third embodiment of the present invention.

Because the third embodiment is almost the same as the first embodiment, only different points are described. The same components are attached with the same symbols, omitting descriptions thereof.

In the above-described first and second embodiments, the scope model image 120 and the display-pause-time image 140 are configured to be changed over in a toggling manner by an ON signal of the change-over switch 40. In the present embodiment, however, the scope model image 120 and the display-pause-time image 140 are changed over based on the shape of the scope model.

Figure 21:
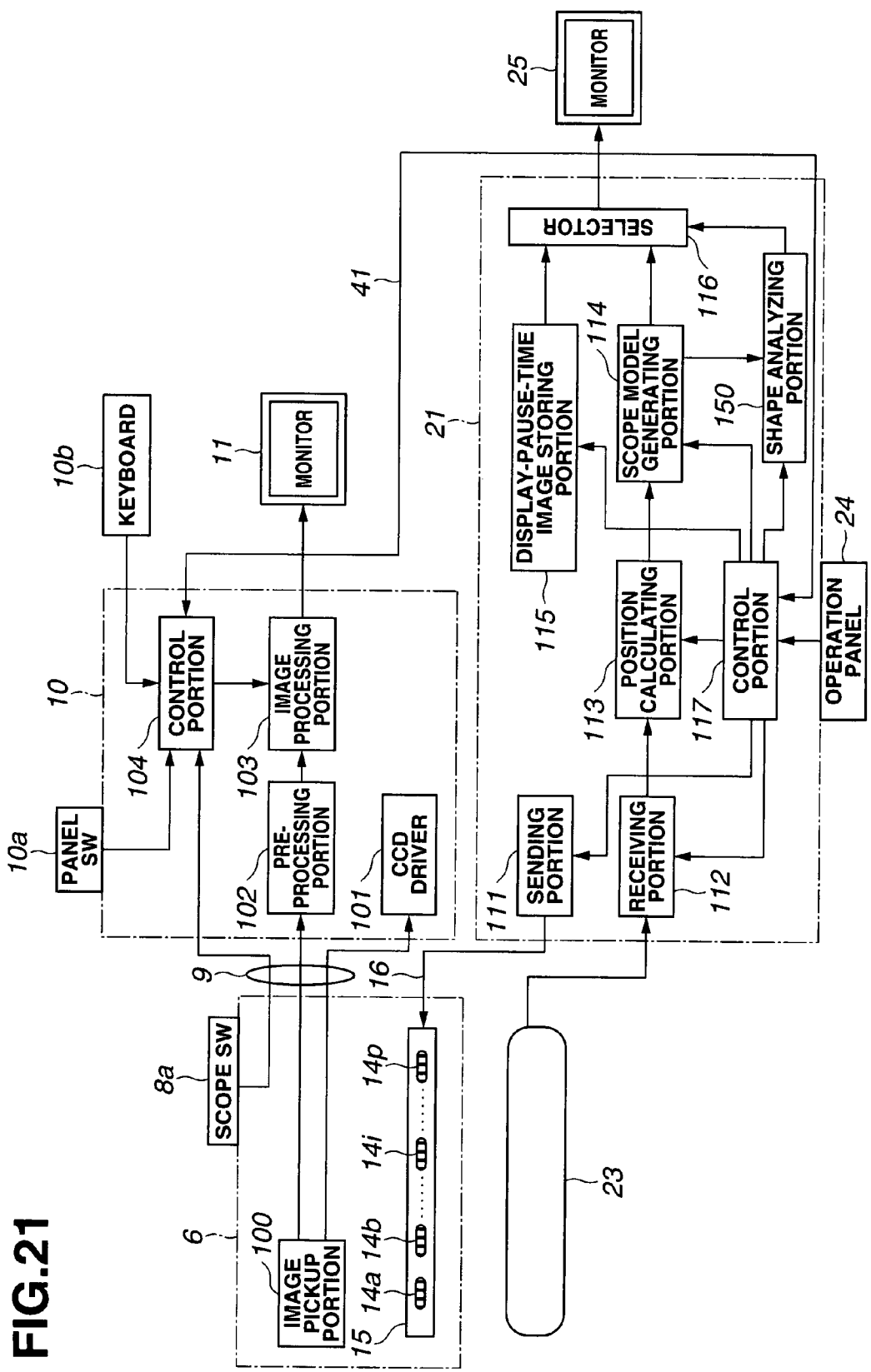
FIG. 21 is a block diagram showing a configuration of a video processor and a detecting apparatus according to a third embodiment of the present invention.

Specifically, in the present embodiment, the detecting apparatus 21a is provided inside with a shape analyzing portion 150 for analyzing the shape of the scope model generated by the scope model generating portion 114, such that the shape analyzing portion 150 switches over the selector 116 based on an analysis result of the shape analyzing portion 150, as shown in FIG. 21.

Figure 22:
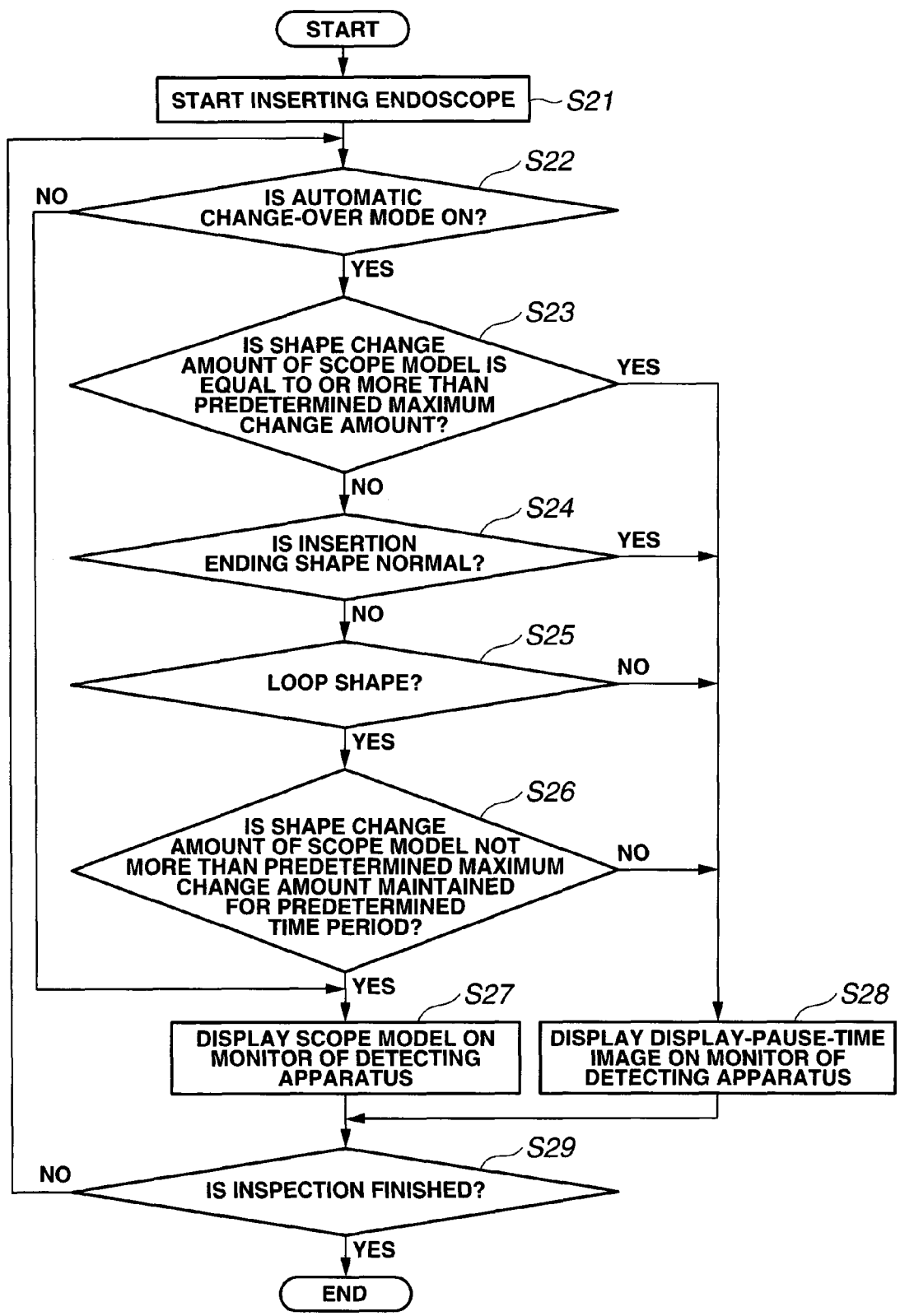
FIG. 22 is a flow chart illustrating processings of the detecting apparatus of FIG. 21.

In the detecting apparatus 21 thus configured, when insertion of the electronic endoscope 2 is started in step S21, the control portion 117 judges whether or not automatic change-over mode is in ON state, in step S22 as shown in FIG. 22. This automatic change-over mode is set to the control portion 117 by the operation panel 24. When the automatic change-over mode is set to ON state, the control portion 117 permits control of the selector 116 based on the analysis result at the shape analyzing portion 150. When the automatic change-over mode is set to OFF state, the control portion 117 prohibits control of the selector 116 based on the analysis result at the shape analyzing portion 150.

Note that, when the automatic change-over mode in OFF state, the control portion 117 sets the selector 116 into a state of outputting a scope model image to the liquid crystal monitor 25, in step S27. This setting of the automatic change-over mode is always possible by means of the operation panel 24.

As such, in step S22, the control portion 117, on judging that the automatic change-over mode is in ON state, causes the shape analyzing portion 150 to perform analysis.

First, in step S23, the shape analyzing portion 150 judges whether or not shape change amount of the scope model 130 is equal to or greater than a predetermined maximum change amount. If judging that a change of equal to or greater than the maximum change amount has occurred with the shape of the scope model 130, the shape analyzing portion 150 judges that the endoscope is favorably inserted, and the process proceeds to step S28.

Here, the shape change amount is calculated by the shape analyzing portion 150 from insertion length of the electronic endoscope 6 and respective coordinate positions of the source coils 14i in the electronic endoscope 6.

Specific behaviors of the shape analyzing portion 150 with respect to the amount of shape change in step S23 are as follows.

1) Obtaining, from the position detecting portion 113, insertion length data of the electronic endoscope 6 and coordinate data of each of the source coils 14i in the electronic endoscope 6.

2) Conducting comparative calculation between the insertion length data of the electronic endoscope 6 and the coordinate data of the source coil 14i, and the same that are previous by a certain amount of time period, so as to obtain a shape change amount.

3) Judging that it is better to display the scope shape, if the time period in which the obtained amount of shape change does not exceed a predetermined value has continued for a predetermined amount of time period or longer.

If judging the shape change amount of the scope model 130 is less than the predetermined maximum change amount, then the shape analyzing portion 150 judges, in step S24, whether or not the insertion state has reached a completion state. For example, the shape analyzing portion 150 judges whether or not the insertion state has reached a completion state, depending on whether or not the shape of the scope model 130 matches a predetermined insertion completion shape. If the shape analyzing portion 150 judges that the insertion state is in a completion state, the process then proceeds to step S28.

Next in step S25, the shape analyzing portion 150 judges whether or not an abnormal loop has occurred with the shape of the scope model 130. If the shape analyzing portion 150 judges there is no abnormal loop, which causes an obstacle for the insertion procedure, the process proceeds to step S28. If the shape analyzing portion 150 judges there is an abnormal loop, the process proceeds to step S26.

In step S26, the shape analyzing portion 150 judges whether or not the state where the shape change of the scope model 130 is not greater than a predetermined minimum change amount has continued for a predetermined amount of time period or more. If the state not greater than the predetermined minimum change amount has continued for the predetermined amount of time period or more, then the processing proceeds to step S27, and if not, to step S28. Here, the abnormal loop indicates a case where the scope is shaped in multiple loops, a loop with an extremely small diameter, and so on.

Specific behaviors of the shape analyzing portion 150 with respect to the abnormal loop in step S26 are as follows.

1) Obtaining respective coordinate data of the source coils 14i in the electronic endoscope 6 from the position detecting portion 113.

2) Conducting comparative calculation among the respective coordinate data of the source coils 14i to obtain scope shape data from the source coils 14i.

3) Judging that it is better to display the scope shape in cases such as where obtained scope shape data indicates a loop shape which is looped multiple times, and where the loop shape is smaller than a predetermined shape (a loop shape to compare with).

In step S27, the shape analyzing portion 150 controls the selector 116 to display the scope model image 120 on the liquid crystal monitor 25. Also, in step S28, the shape analyzing portion 150 controls the selector 116 to display the display-pause-time image 140 on the liquid crystal monitor 25.

The shape analyzing portion 150 then repeats the processings of the above steps S22 to S28 until the inspection is finished in step S29.

If, in the above-mentioned processings, the insertion of the electronic endoscope is delayed for a predetermined time period, then the shape analyzing portion 150 judges that insertion support is necessary and displays the scope model 120 on the liquid crystal monitor 25. If not, the shape analyzing portion 150 judges that insertion support is not necessary and displays the display-pause-time image 140 on the liquid crystal monitor 25.

Figure 23:
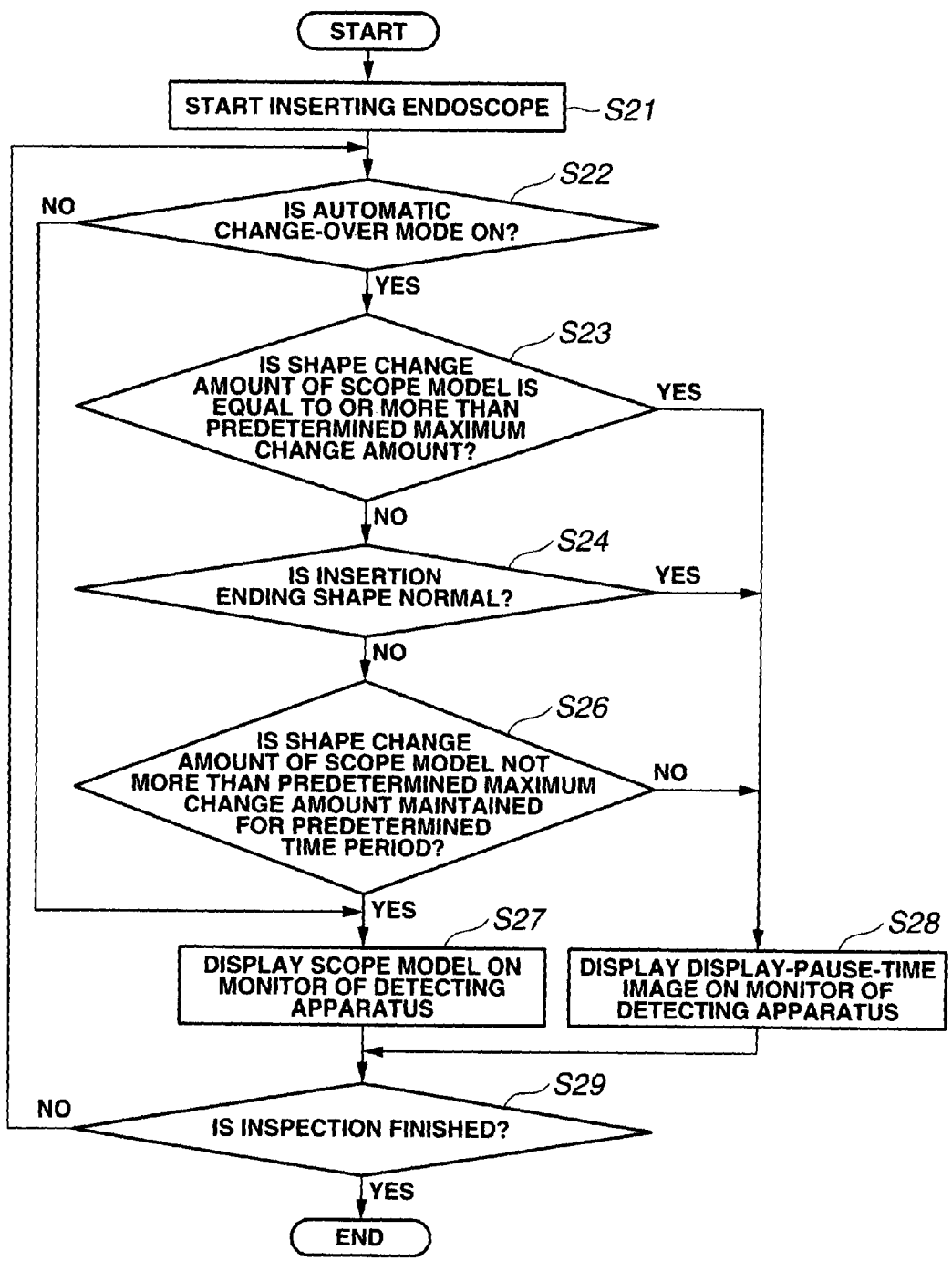
FIG. 23 is a flow chart showing a modification example of the processings of FIG. 22.

Note that, even if no abnormal loop has occurred, in a case where the state where the shape change of the scope model 130 is not greater than the predetermined minimum change amount has continued for a predetermined amount of time period or more, which in some cases needs insertion support, the processing of the above step S25 (abnormal loop detection processing) may be omitted, as shown in FIG. 23.

Thus, in the present embodiment, the scope model display is controlled to be switched on/off based on the analysis result of the shape analyzing portion 150, which allows displaying the insertion shape of the endoscope at a timing as needed based on the insertion shape.

Furthermore, in the present embodiment, if the state of the electronic endoscope 6 is judged to conclude it is desirable to display the shape thereof, the shape is automatically displayed. This permits the operator to concentrate on the scope operation without being bothered by operating the display.

Figure 24:
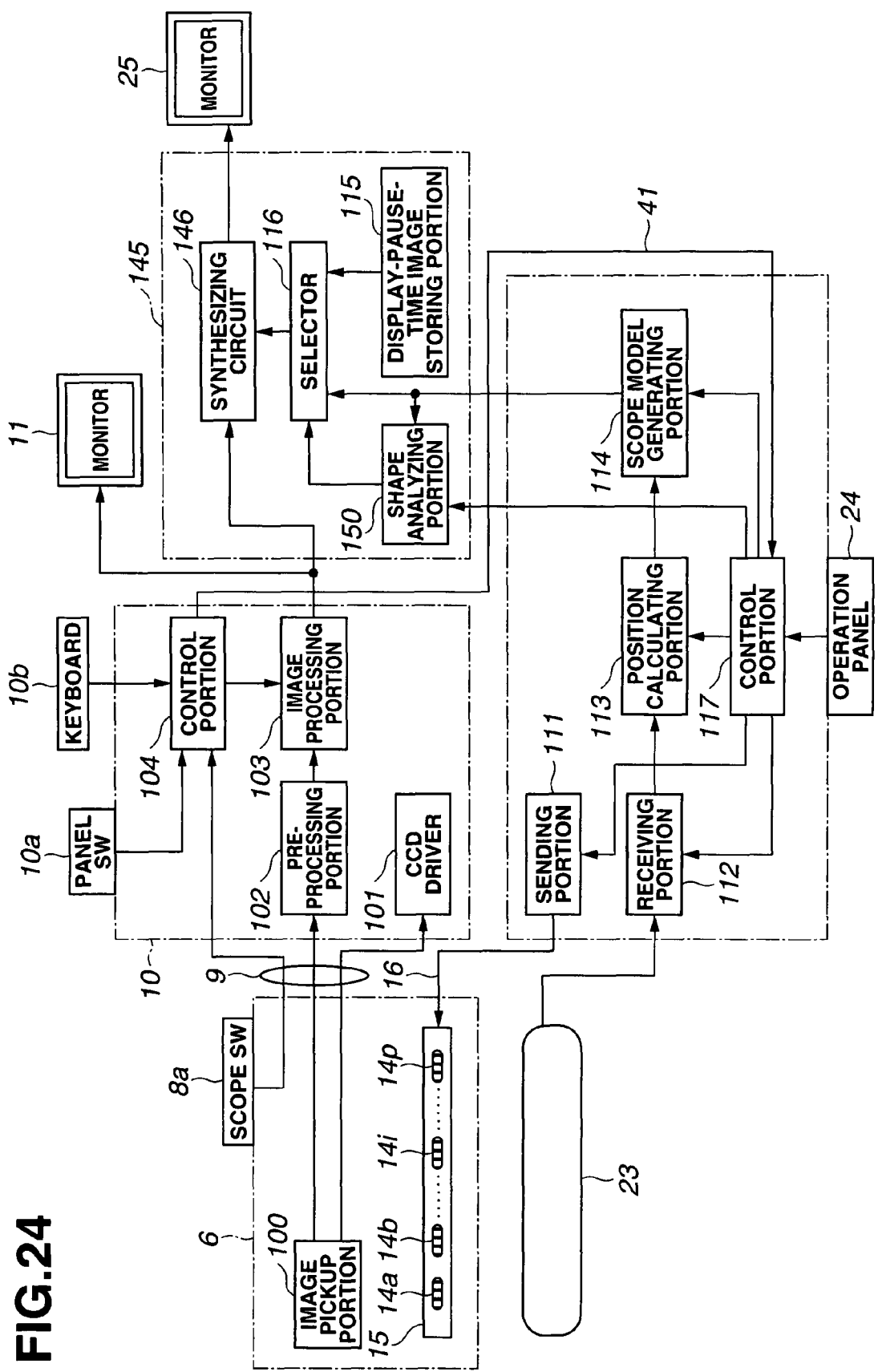
FIG. 24 is a block diagram showing a configuration of a modification example of the video processor and the detecting apparatus of FIG. 21.

Note that, in the present embodiment as in the second embodiment, the image synthesizing apparatus 145 may be provided inside with the shape analyzing portion 150 along with the display-pause-time image storing portion 115, the selector 116, and the synthesizing circuit 146, as shown in FIG. 24.

Fourth Embodiment

Figure 25:
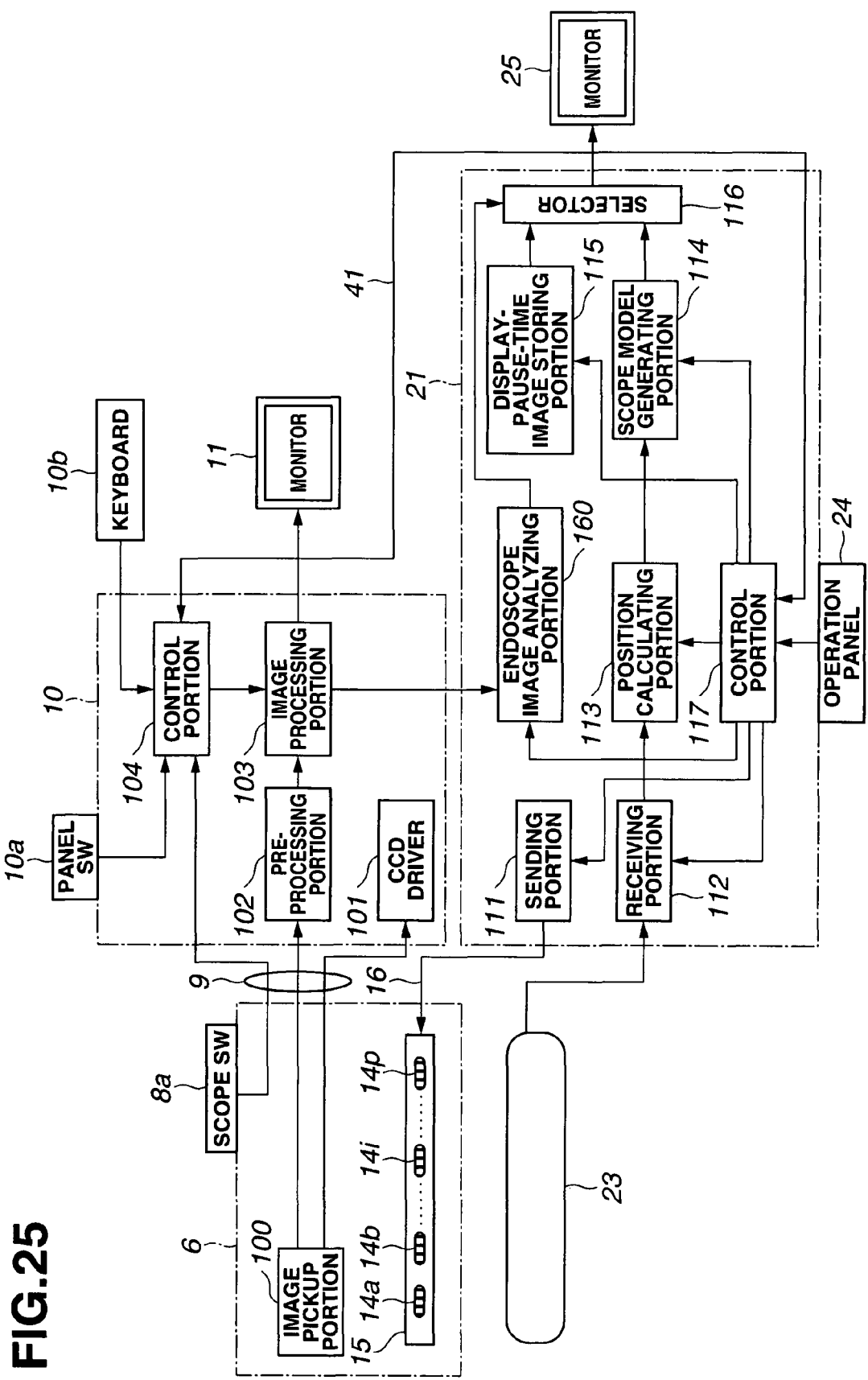
FIG. 25 is a block diagram showing a configuration of a video processor and a detecting apparatus according to a fourth embodiment of the present invention.
Figure 26:
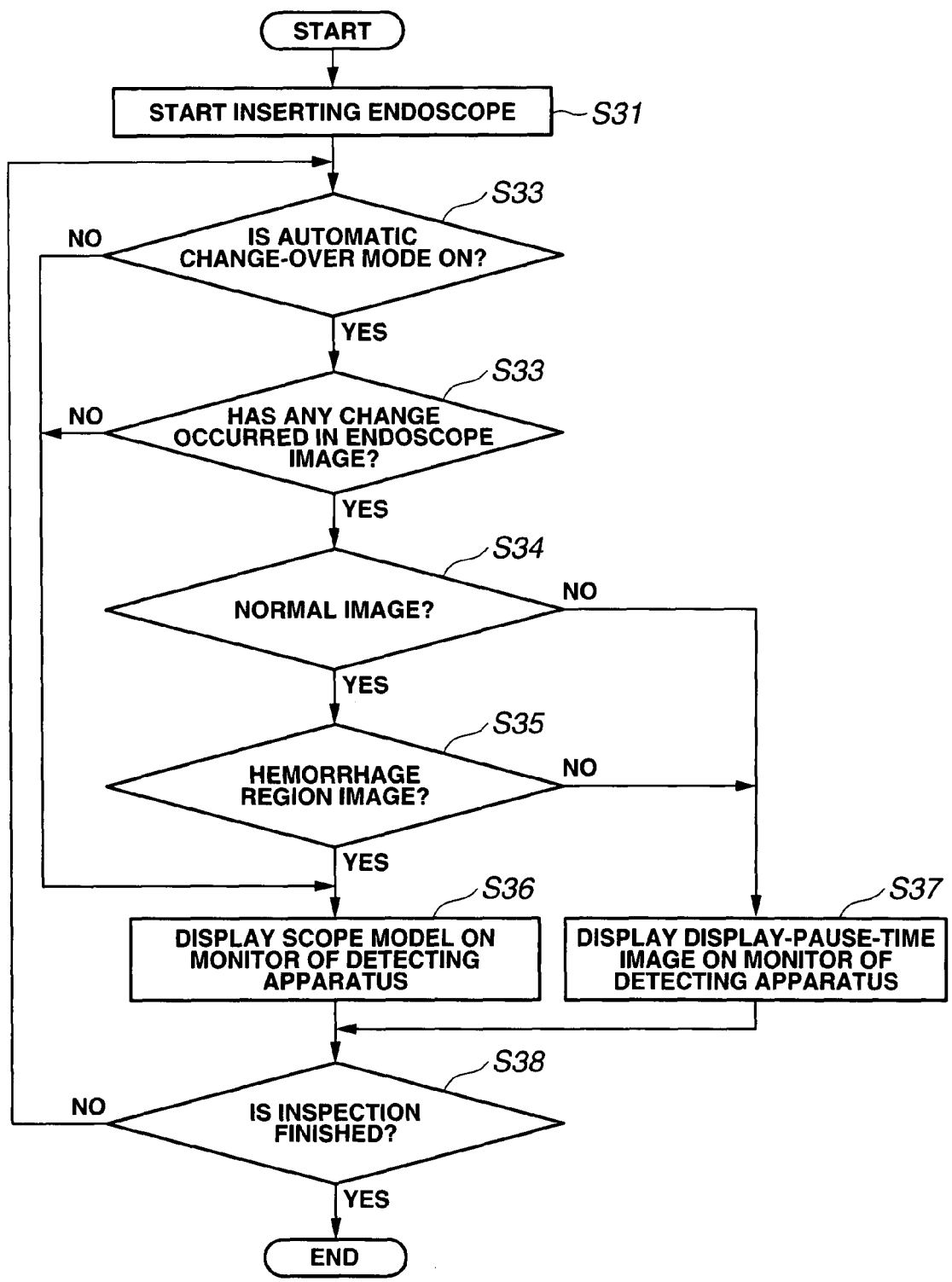
FIG. 26 is a flow chart illustrating processings of the detecting apparatus of FIG. 25.
Figure 27:
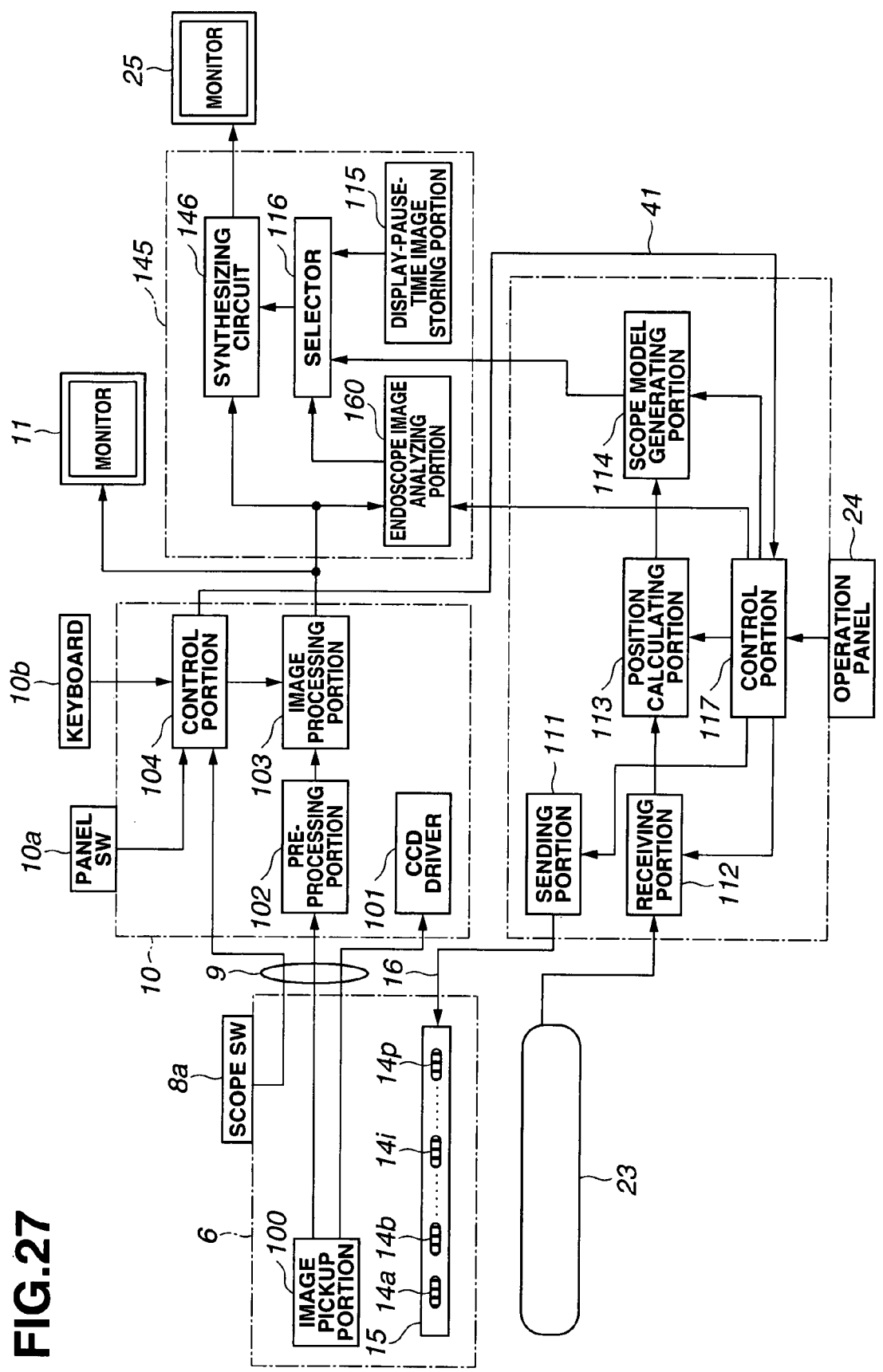
FIG. 27 is a block diagram showing a configuration of a modification example of the video processor and the detecting apparatus of FIG. 25.

FIGS. 25 to 27 show a fourth embodiment of the present invention.

Because the fourth embodiment is almost the same as the third embodiment, only different points are described. The same components are attached with the same symbols, omitting descriptions thereof.

In the third embodiment, the scope model 120 is displayed on the liquid crystal monitor 25, if analyzing the shape of the scope model (insertion state of the electronic endoscope) results in a judgment as a state needing insertion support. In the present embodiment, however, the scope model 120 is displayed on the liquid crystal monitor 25, if analyzing the endoscope image concludes that the endoscope image needs insertion support.

Specifically, in the present embodiment, the detecting apparatus 21 is provided inside with an endoscope image analyzing portion 160 for analyzing an endoscope image from the image processing portion 103 of the video processor 10, such that the endoscope image analyzing portion 160 switches over the selector 116 based on an analysis result of the endoscope image analyzing portion 160, as shown in FIG. 25.

In the detecting apparatus 21 thus configured, when insertion of the electronic endoscope 2 is started in step S31, the control portion 117 judges in step S32 as to whether or not the automatic change-over mode is in ON state, as shown in FIG. 26. This automatic change-over mode is set with respect to the control portion 117 by the operation panel 24. When the automatic change-over mode is set to ON state, the control portion 117 permits control of the selector 116 based on the analysis result at the endoscope image analyzing portion 160. When the automatic change-over mode is set to OFF state, the control portion 117 prohibits control of the selector 116 based on the analysis result at the endoscope image analyzing portion 160.

Note that, when the automatic change-over mode in OFF state, the control portion 117 sets the selector 116 into a state of outputting a scope model image to the liquid crystal monitor 25, in step S36. This setting of the automatic change-over mode is always possible by means of the operation panel 24.

As such, the control portion 117, on judging in step S32 that the automatic change-over mode is in ON state, causes the endoscope image analyzing portion 160 to perform analysis.

First, in step S33, the endoscope image analyzing portion 160 judges whether or not there is a change in the endoscope image being observed. If there is no change in the endoscope image being observed, the processing proceeds to step S36. If there is a change in the endoscope image being observed, the processing proceeds to step S34.

In step S34, the endoscope image analyzing portion 160 judges by, for example, luminance analysis, as to whether the change of the endoscope image is one due to abnormality such as halation or a normal state of change of the endoscope image. If the change of the endoscope image is judged as one in a normal image, the processing proceeds to step S35. If the change of the endoscope image is judged as one due to abnormality such as halation, the processing proceeds to step S37.

Here, the luminance analysis by the endoscope image analyzing portion 160 is performed in a case such as where the entire image has become dark in a state such as where a scope distal end portion is in close contact with an intestine wall.

In step S35, the endoscope image analyzing portion 160 judges by, e.g., color tone analysis whether or not the endoscope image is a hemorrhage region image showing occurrence of hemorrhage. If the endoscope image is judged as a hemorrhage region image, the processing proceeds to step S36. If the endoscope image is not judged as a hemorrhage region image, the processing proceeds to step S37.

Here, the color tone analysis at the endoscope image analyzing portion 160 analyzes a concentrated region of highly pure red ingredient such as in a hemorrhage region, and so forth.

In step S36, the endoscope image analyzing portion 160 controls the selector 116 to display the scope model image 120 on the liquid crystal monitor 25. In step S37, the endoscope image analyzing portion 160 controls the selector 116 to display the display-pause-time image 140 on the liquid crystal monitor 25.

The endoscope image analyzing portion 160 repeats the processings of the above steps S32 to S37 until the inspection is finished in step S38.

Thus, in the present embodiment, the switching on/off of the display of the scope model is controlled based on the analysis result of the endoscope image analyzing portion 160, thus allowing the insertion shape of the endoscope to be displayed at a timing as needed based on the endoscope image.

Note that, in the present embodiment as in the second embodiment, the image synthesizing apparatus 145 may be provided inside with the endoscope image analyzing portion 160 along with the display-pause-time image storing portion 115, the selector 116, and the synthesizing circuit 146, as shown in FIG. 27.

The present invention is not limited to the above-mentioned embodiments, but various changes, modifications or the like are possible within a scope not changing the spirit of the present invention.

This application is filed claiming priority from Japanese Patent Application No. 2005-120043 applied in Japan on Apr. 18, 2005, the disclosed contents of which being incorporated in the present specification, claims, and drawings.

The invention claimed is:

1. An endoscope shape detecting apparatus comprising:
   a device detecting portion comprising:
   one of a group of a plurality of magnetic field generating devices and a group of a plurality of magnetic field detecting devices disposed inside an insertion portion of an endoscope to be inserted into a subject; and
   the other of the groups of devices being disposed outside the subject,
   wherein the device detecting portion is configured to detect respective positions of the one group of devices disposed inside the insertion portion by using positions of the other group of devices as reference;
   a monitor comprising a screen, wherein the monitor is configured to display an endoscope image obtained by the endoscope on the screen, and to selectively display a model image of a shape of the insertion portion of the endoscope; and
   a processor comprising hardware, wherein the processor is configured to:
   estimate the shape of the insertion portion of the endoscope based on the respective positions detected by the device detecting portion;
   generate the model image of the estimated shape of the insertion portion of the endoscope;
   perform image analysis on the endoscope image obtained by the endoscope;
   judge whether a predetermined condition occurred based on at least one of the estimated shape of the insertion portion of the endoscope and a result of the image analysis on the endoscope image; and
   control the monitor to automatically display the model image with the endoscope image on the screen of the monitor upon judgment that the predetermined condition occurred.

2. The endoscope shape detecting apparatus according to claim 1, wherein the processor is configured to judge that the predetermined condition occurred by determining at least one of:
   a change amount of the shape of the insertion portion is less than a predetermined maximum change amount,
   an abnormal loop which causes an obstacle for an insertion operation of the insertion portion has occurred with the shape of the insertion portion,
   a state where change in the shape of the insertion portion is not greater than a predetermined minimum change amount has continued for a predetermined time period or more, and
   there is no change in the endoscope image.

3. The endoscope shape detecting apparatus according to claim 1, further comprising a switch configured to:
   be switched by an operator between a first state and a second state,
   output a first signal to the processor when in the first state, and
   output a second signal to the processor when in the second state,
   wherein the processor is further configured, upon receiving the first signal, to control the monitor to automatically display the model image with the endoscope image on the screen of the monitor upon judgment that the predetermined condition occurred, and
   wherein the processor is further configured, upon receiving the second signal, to prohibit control of the monitor to automatically display the model image with the endoscope image on the screen of the monitor.

* * * * *